(12) United States Patent
Qian

(10) Patent No.: US 11,457,860 B2
(45) Date of Patent: Oct. 4, 2022

(54) HUMAN-COMPUTER INTERACTIVE DEVICE AND METHOD

(71) Applicant: Cheng Qian, Weston, FL (US)

(72) Inventor: Cheng Qian, Weston, FL (US)

(73) Assignee: Cheng Qian, Weston, FL (US)

( * ) Notice: Subject to any disclaimer, the term of this patent is extended or adjusted under 35 U.S.C. 154(b) by 274 days.

(21) Appl. No.: 16/505,481

(22) Filed: Jul. 8, 2019

(65) Prior Publication Data

US 2020/0008739 A1 Jan. 9, 2020

Related U.S. Application Data

(60) Provisional application No. 62/695,542, filed on Jul. 9, 2018.

(51) Int. Cl.
*A61B 5/00* (2006.01)
*A61B 5/374* (2021.01)
*A61B 5/291* (2021.01)
*A61B 5/398* (2021.01)

(52) U.S. Cl.
CPC ........... *A61B 5/4806* (2013.01); *A61B 5/291* (2021.01); *A61B 5/374* (2021.01); *A61B 5/6803* (2013.01); *A61B 5/6814* (2013.01)

(58) Field of Classification Search
CPC ....... A61B 5/4806; A61B 5/291; A61B 5/374; A61B 5/6803; A61B 5/6814; A61B 5/4812; A61B 5/4815; A61B 5/6831; A61B 5/398; A61B 5/4809; G06F 3/015
See application file for complete search history.

(56) References Cited

U.S. PATENT DOCUMENTS

| | | | |
|---|---|---|---|
| 6,270,466 B1 * | 8/2001 | Weinstein | A61B 5/6816 600/590 |
| D709,673 S | 7/2014 | Aimone et al. | |
| 9,563,273 B2 | 2/2017 | Mann | |
| 9,764,110 B2 | 9/2017 | Larson et al. | |
| 9,820,670 B2 | 11/2017 | Parvizi et al. | |
| D824,523 S | 7/2018 | Paoli et al. | |
| 10,120,413 B2 | 11/2018 | Aimone et al. | |
| 10,285,646 B1 | 5/2019 | Grant et al. | |
| 2007/0055169 A1 * | 3/2007 | Lee | A61B 5/0015 600/544 |
| 2007/0249952 A1 * | 10/2007 | Rubin | A61B 5/4812 600/544 |
| 2009/0082829 A1 * | 3/2009 | Panken | A61N 1/36139 607/45 |
| 2010/0234697 A1 * | 9/2010 | Walter | A61B 5/291 600/301 |
| 2010/0234752 A1 * | 9/2010 | Sullivan | A61B 5/165 600/544 |

(Continued)

*Primary Examiner* — Devin B Henson
*Assistant Examiner* — Justin Xu
(74) *Attorney, Agent, or Firm* — Metis IP LLC

(57) ABSTRACT

The present disclosure relates to a bioelectrical signal acquisition device, an interactive system, and related methods. The bioelectrical signal acquisition device includes a series of electrodes that are configured and positioned to effectively record bioelectrical signals from a user's head. The interactive system and related methods can be used to collect, display, and analyze the bioelectrical signals, especially signals related to sleep. The device, system, and methods can also be applied to modulate physiological or pathological conditions of the user.

13 Claims, 24 Drawing Sheets

(56) References Cited

U.S. PATENT DOCUMENTS

| | | | |
|---|---|---|---|
| 2015/0011857 A1* | 1/2015 | Henson | A61B 5/6831 |
| | | | 600/383 |
| 2016/0317056 A1* | 11/2016 | Moon | A61B 5/6803 |
| 2017/0055868 A1* | 3/2017 | Hatakeyama | A61B 3/0025 |
| 2017/0164903 A1 | 6/2017 | Soulet De Brugiere et al. | |
| 2018/0081433 A1* | 3/2018 | Nandaragi | G06F 3/0482 |
| 2018/0133431 A1* | 5/2018 | Malchano | A61B 5/0036 |
| 2019/0033914 A1 | 1/2019 | Aimone et al. | |
| 2019/0070386 A1 | 3/2019 | Raut et al. | |
| 2019/0142335 A1* | 5/2019 | Garcia Molina | A61B 5/7235 |
| | | | 340/575 |
| 2021/0259601 A1* | 8/2021 | Kornberg | G06F 3/0304 |

* cited by examiner

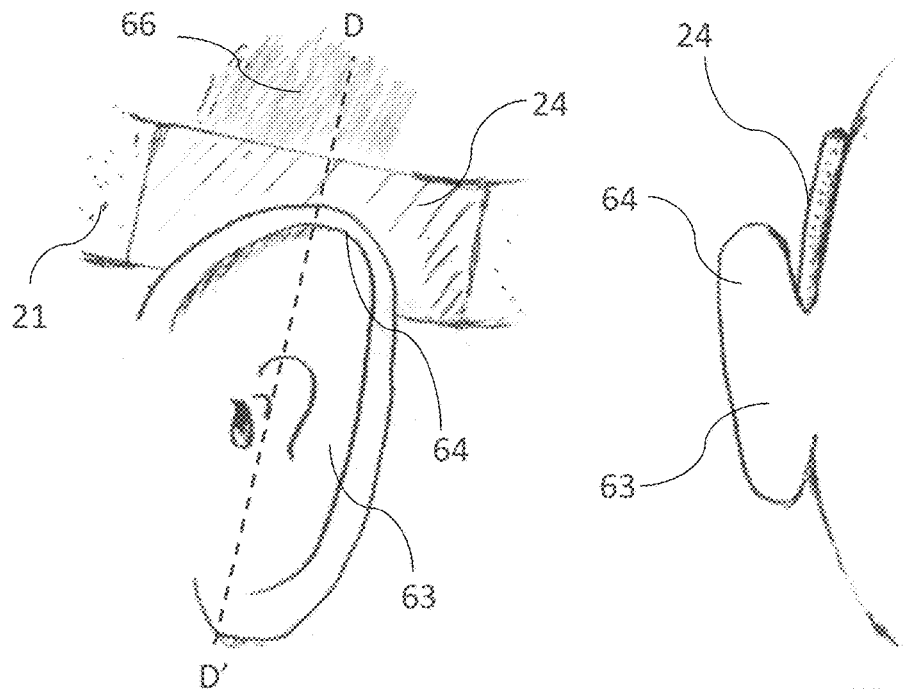
FIG. 3A
FIG. 3B
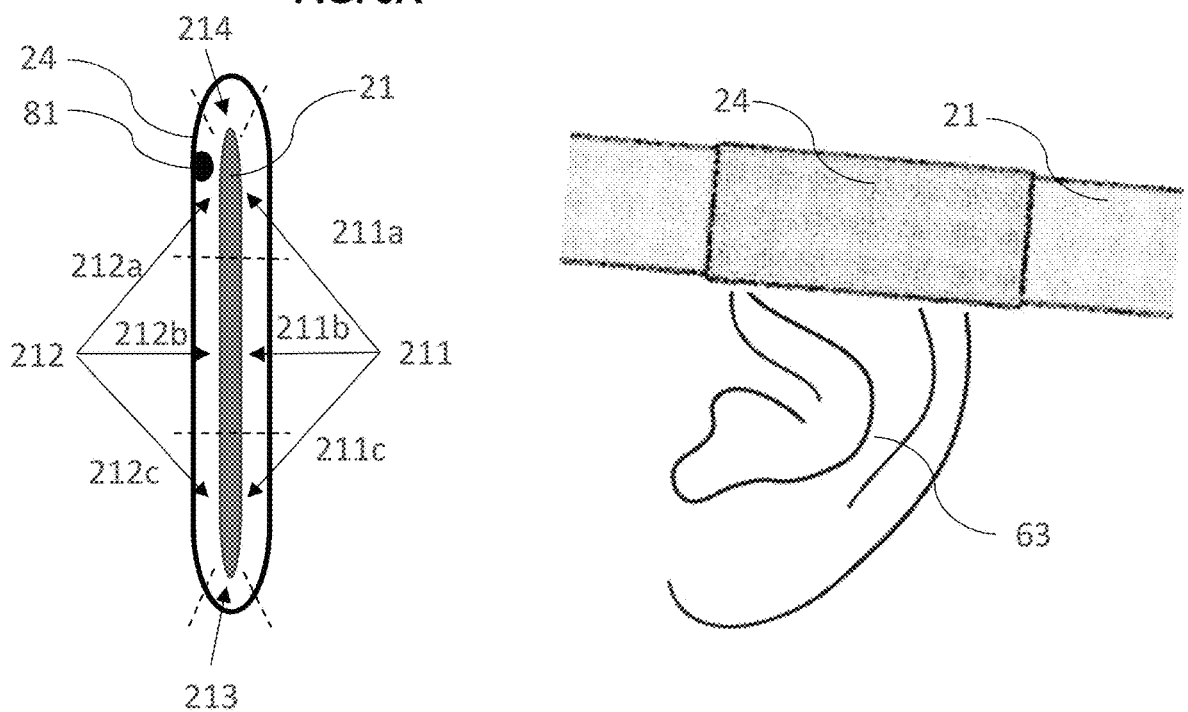
FIG. 3C
FIG. 3D

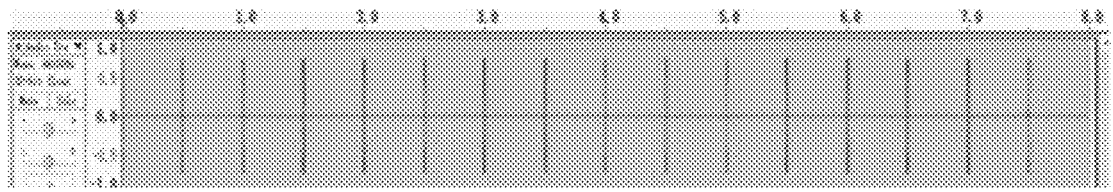
FIG. 9B
FIG. 9C
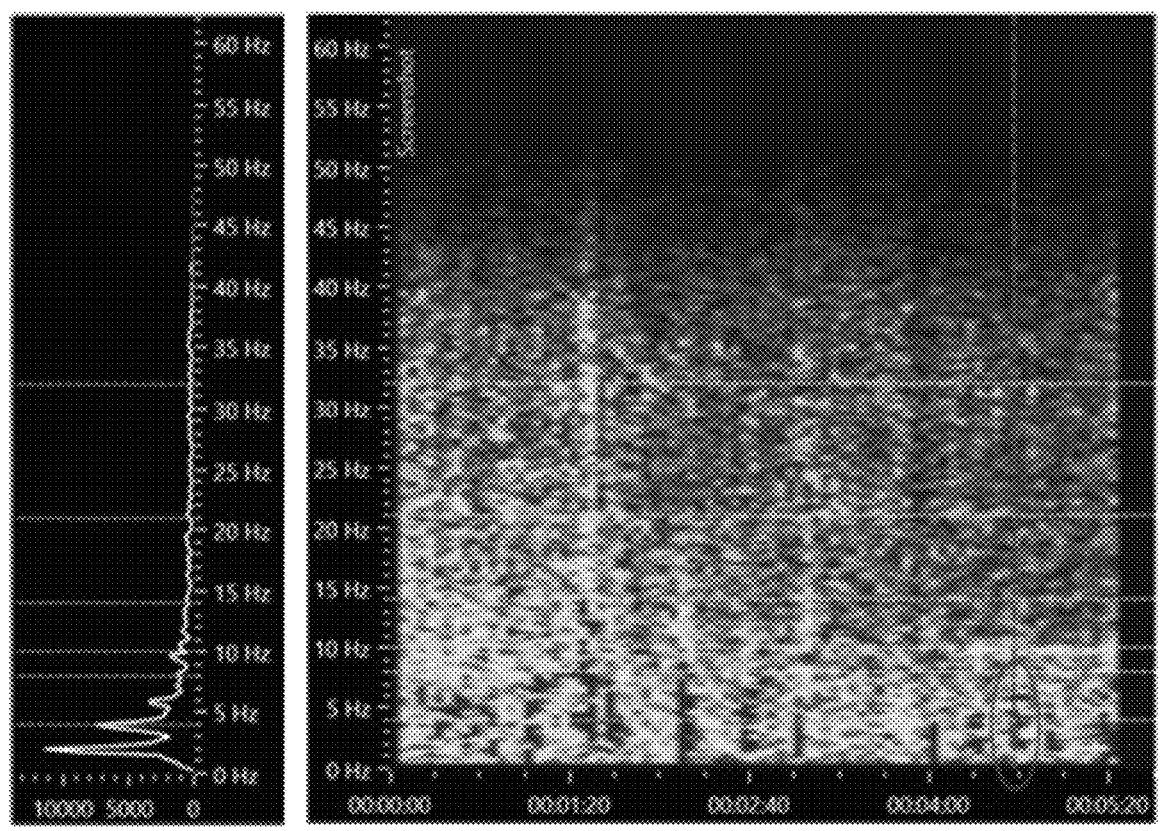
FIG. 9D                    FIG. 9E

HUMAN-COMPUTER INTERACTIVE DEVICE AND METHOD

CROSS-REFERENCE TO RELATED APPLICATIONS

This application claims priority to U.S. Provisional Patent Application No. 62/695,542, filed on Jul. 9, 2018, the entire contents of which are hereby incorporated by reference.

TECHNICAL FIELD

The present disclosure relates to devices, systems, and methods that can be used in acquiring, measuring, and processing bioelectrical signals, with extensive applications in monitoring, analysis and/or modulation of various physiological conditions, such as but not limited to sleep-monitoring, sleep pattern analysis, sleep-assistance, and other types of functions involving human-computer interactions.

BACKGROUND

Bioelectrical signals are generated by biological subjects and can be collected and processed. Such signals, and the patterns formed thereof, are being used to monitor, diagnose, and manipulate physiological and pathological conditions. Electroencephalogram (EEG), electromyogram (EMG), and electrooculography (EOG) signals are some typical examples of bioelectrical signals.

In recent years, various types of devices and apparatus have been developed to monitor bioelectrical signals, especially in the field of sleep monitoring. However, the devices and apparatus almost invariably face the problem of causing discomfort to the human subjects, typically by making it more difficult for them to fall asleep or disturbing the sleep patterns. Therefore, it is desirable to provide devices that can effectively collect and process bioelectrical signals, with minimum disturbance to the subjects regarding their physiological functions, such as sleep. In addition, it also would be desirable that such devices are small, portable, wearable, wirelessly, and easy to use.

In some instances, measuring bioelectrical signals entails further interaction with the human subject. However, common interactive behaviors by the subject, such as looking at and touching screens and/or monitors, are disruptive if the subject is trying to fall asleep. When the human subject has been lying comfortably on bed, with eyes closed and is ready for sleep, body movements and exposure to light from the screens would negatively affect sleep onset and sleep quality. Therefore, it would be ideal to interact with the subject with minimum intrusion. For sleep-assisting devices, sleep-recording devices, and associated methods, it is desirable that the human subject can carry out control or interact with the devices with as little action as possible, ideally without even opening their eyes or moving any major body parts.

SUMMARY

In one aspect, the present disclosure related to providing devices and methods for monitoring human physiological and pathological conditions. In some embodiments, the present disclosure related to providing devices and methods for monitoring sleep.

In another aspect, the present disclosure relates to providing devices and methods for modulating human physiological and pathological conditions. In some embodiments, the present disclosure relates to providing devices and methods modulating sleep (e.g., sleep assistance).

In another aspect, the present disclosure relates to providing devices and methods that balance comfort and effectiveness in recording signals from a user's head.

In another aspect, the present disclosure relates to providing devices and methods that allows for effective interaction with a user that is trying to fall asleep. In some embodiments, the present disclosure relates to providing devices and methods that allows for effective interaction with a user without the user opening his/her eyes.

In another aspect, the present disclosure relates to providing devices and methods that allows people to control a computational device without looking at a screen or moving a finger, hand, limb, or mouth.

In some embodiments, the present disclosure relates to a 1. A bioelectrical signal acquisition device, comprising: a headband configured to be wearable around a user's head, a sensing electrode attached to the headband; a reference electrode attached to the headband; wherein the sensing electrode and the one or more reference electrodes are configured to provide sensing signals from the user's head, and the reference electrode is configured to cover at least part of a bottom side of a segment of the headband, and a processing unit configured to generate digital bioelectrical signals based on the sensing signals. In some embodiments, the bioelectrical signal acquisition device further includes a grounding electrode.

In some embodiments, the present disclosure relates to an interactive system, comprising: a bioelectrical signal acquisition device, and a computational unit configured to receive the digital bioelectrical signals from the bioelectrical signal acquisition device, process the digital bioelectrical signals and execute one or more logic sets based on the digital bioelectrical signals.

In some embodiments, the present disclosure relates to method of monitoring sleep patterns of a user, comprising: providing an interactive system; collecting the digital bioelectrical signals of the user with the bioelectrical signal acquisition device when the user sleeps or prepares to fall asleep; and processing the digital bioelectrical signals with the computational unit to monitor the sleep patterns of the user.

In some embodiments, the present disclosure relates to a method of human-computer interaction using an interactive system, comprising: providing a signal sequence to the user; recording digital bioelectrical signals from the user's head using a bioelectrical signal acquisition device; processing the digital bioelectrical signals and identifying the existence and the pattern of ocular event-related potentials (o-ERPs); and taking one or more actions based on the existence and the patterns of the o-ERPs.

In some embodiments, the present disclosure relates to a method of detecting o-ERPs, comprising: recording digital bioelectrical signals from the user's head using a bioelectrical signal acquisition device; and processing the digital bioelectrical signals with a computational unit and identifying the existence and the pattern of o-ERPs.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The devices, systems, methods, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 1A-1G show different views of an exemplary bioelectrical signal acquisition device according to some embodiments of the present disclosure; FIG. 1A is a perspective view thereof; FIG. 1B is a bottom planform view thereof; FIG. 1C is a top planform view thereof; FIG. 1D is a first side view thereof; FIG. 1E is a second side view thereof; FIG. 1F is a first end view thereof; FIG. 1G is a second end view thereof.

FIG. 3A-3D are diagrams illustrating positioning of the reference electrode around a user's ear according to some embodiments of the present disclosure; FIG. 3A shows a side view of the a user's ear when the reference electrode is positioned above the user's ear; FIG. 3B shows a back view of the user's ear and head when the reference electrode is positioned above a user's ear; FIG. 3C shows a sectional view of the reference electrode and the headband; FIG. 3D shows a side view of the a user's ear when the reference electrode is positioned over the user's ear.

FIG. 4A is a block diagram showing that the interactive system includes the bioelectrical signal acquisition device, a computational unit, and a notice unit according to some embodiments of the present disclosure; FIG. 4B is a diagram showing that in the interactive system according to certain embodiments of the present disclosure, where the computational unit and the bioelectrical signal acquisition device may be integrated; FIG. 4C is a diagram showing that in the interactive system according to certain embodiments of the present disclosure, where the computational unit is a generic microcontroller; FIG. 4D is a diagram showing that in the interactive system according to certain embodiments of the present disclosure, where the computational unit is a separate computing device.

FIG. 5A shows simplified and basic wiring of an interactive system including wired connection with the notice unit; FIG. 5B shows simplified and basic wiring of an interactive system including wireless connection with the notice unit.

FIG. 6A show various types of brainwave data acquired by the bioelectrical signal acquisition device according to some embodiments of the present disclosure; FIG. 6B shows a frequency-domain signal presentation of a user before, during and after a sleep onset process by the bioelectrical signal acquisition device according to some embodiments of the present disclosure; FIG. 6C shows a frequency-domain signal presentation of a user during a full night of sleep by the bioelectrical signal acquisition device according to some embodiments of the present disclosure.

FIG. 8A is a flowchart of the process according to some embodiments of the present disclosure; FIG. 8B is time-domain signal presentation, or wave chart; FIG. 8C shows a frequency-domain presentation, or a spectrogram.

FIG. 9A-9E show an exemplary process of human-computer interaction and the recorded signals according to some embodiments of the present disclosure; FIG. 9A is a flowchart of the process according to some embodiments of the present disclosure; FIG. 9B shows an audio template at a pace of twice per second; FIG. 9C is time-domain signal presentation, or wave chart, with sequence of synchronized o-ERPs; FIG. 9D shows a frequency histogram with a peak at 2 Hz; FIG. 9E shows a frequency-domain presentation, or a spectrogram, with a bright spot at 2 Hz.

FIG. 12A is a flowchart of the process according to some embodiments of the present disclosure; FIG. 12B is time-domain signal presentation, or wave chart; FIG. 12C provides an alternative process similar to the process shown in FIG. 12A.

FIG. 13A is a flowchart of the process according to some embodiments of the present disclosure; FIG. 13B is time-domain signal presentation, or wave chart.

DETAILED DESCRIPTION

Figure 1A:
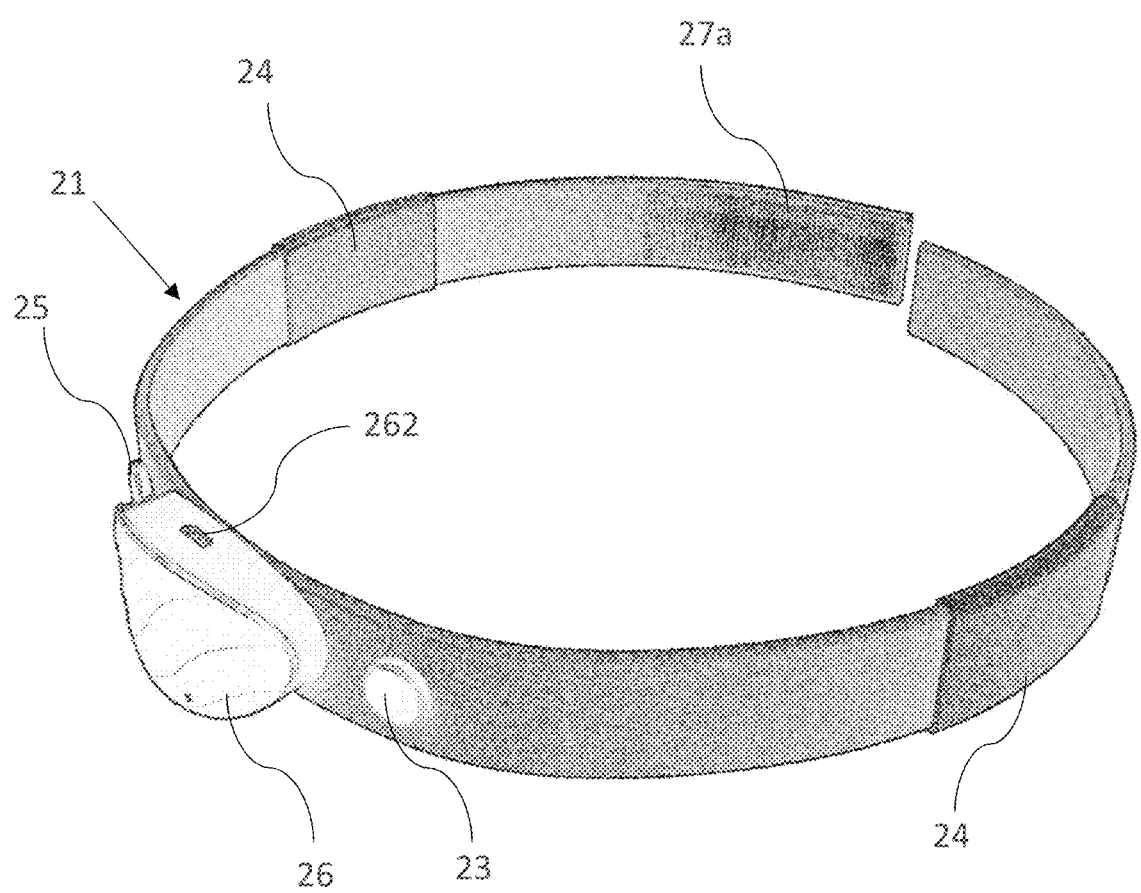

In the following detailed description, numerous specific details are set forth by way of examples in order to provide a thorough understanding of the relevant teachings. However, it should be apparent to those skilled in the art that the present disclosure may be practiced without such details. In other instances, well known methods, procedures, systems, components, and/or circuitry have been described at a relatively high level, without detail, in order to avoid unnecessarily obscuring aspects of the present disclosure.

The present disclosure describes bioelectrical signal acquisition devices, interactive system, as well as methods for collecting, measuring, recording, analyzing, and utilizing bioelectrical signals from biological beings, including but not limited to human subjects. In some embodiments, the devices, systems, and methods herein described can be used in studying, analyzing, and manipulation of physical conditions and functions. For example, the devices, systems, and methods herein described can be used to study and intervene with sleep and functions associated with sleep, such as but not limited to sleep onset, sleep depth, sleep dynamics, dream, memory consolidation, physical recovery, insomnia, sleep apnea, narcolepsy, hypersomnia, and abnormal sleep structure.

The devices, systems and methods herein disclosed may also be used to study and modulate a user's mental status, such as but not limited to anxiety, depression, attention deficiency, stress and meditation. The devices, systems and methods herein disclosed may be convenient and effective tools to assess the effectiveness of sleep treatments, pharmaceutical, physical, cognitive or behavioral. They may also be used in neurofeedback to intervene and make adjustments based on the user's neurological and mental conditions. They can be used as a two-way communication system allowing the user in certain physiological conditions, such as dream state or in pseudo-coma, also known as "locked-up syndrome", to send signal voluntarily with specific eye movements so that he or she can effectively interact with the surrounding environment.

The present disclosure also relates to the ornamental design for a bioelectrical signal acquisition device or a portion thereof, as shown and described in association with the Figures.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood that the operations of the flowchart may be implemented not in order. Conversely, the operations may be implemented in inverted order, or simultaneously. Moreover, one or more other operations may be added to the flowcharts. One or more operations may be removed from the flowcharts.

In the present disclosure, the term "bioelectrical signal" refers to electric signals produced by biological beings, such as but not limited to plants and animals. In some embodiments, the bioelectrical signals of the present disclosure are produced by a human subject.

In the present disclosure, the term "user" refers to a subject using the bioelectrical signal acquisition device and/or the interactive system of the present disclosure. Here "using" means wearing and/or being tested, monitored or analyzed. In some embodiments, the user is a human being. In some embodiments, the user is an animal other than a human being. In some embodiments, the bioelectrical signal acquisition device is configured to be worn on the user's head. In some embodiments, the bioelectrical signal acquisition device is configured to be worn on other body parts, such as but not limited to chest, leg, foot, arm, hand, neck, shoulder, hip, and back. In some embodiments, the user is a male or a female. In some embodiments, the user is a newborn, an infant, a toddler, a child, a teenager, a young adult, an adult, or a senior.

In the present disclosure, the bioelectrical signal acquisition device, the interactive system, and the methods herein disclosed are used to test, monitor, and/or analyze certain physiological or pathological conditions and/or functions. In some embodiments, the bioelectrical signal acquisition device, the interactive system, and the methods herein disclosed are used to test, monitor, and/or analyze sleep and related conditions and/or functions.

In the present disclosure, the term "sleep" or "asleep" refers to a condition of body and mind such as that which typically recurs for several hours every night, in which the nervous system is relatively inactive, the eyes closed, the postural muscles relaxed, and consciousness practically suspended. The devices, systems, and methods of the present disclosure can be used for collecting, monitoring, and analyzing digital bioelectrical signals from a user when the user is sleeping or in a sleep-related stage. In certain embodiments, the user is preparing to fall asleep. In certain embodiments, the user is asleep. In certain embodiments, the user is experiencing different stages of sleeping, including but not limited to stage 1 sleep, stage 2 sleep, stage 3 sleep, and rapid eye movement (REM) sleep. In certain embodiments, the user is in an awake stage (wake up time in the morning) immediately after a period of sleep. In certain embodiments, the user is in an awake stage between two close periods of sleep. In some embodiments, the user goes through a duration that combines some or all of the stages related to sleep.

FIGS. 1A-1G show different views of an exemplary bioelectrical signal acquisition device 20 according to some embodiments of the present disclosure.

Figures 1B, 1C:
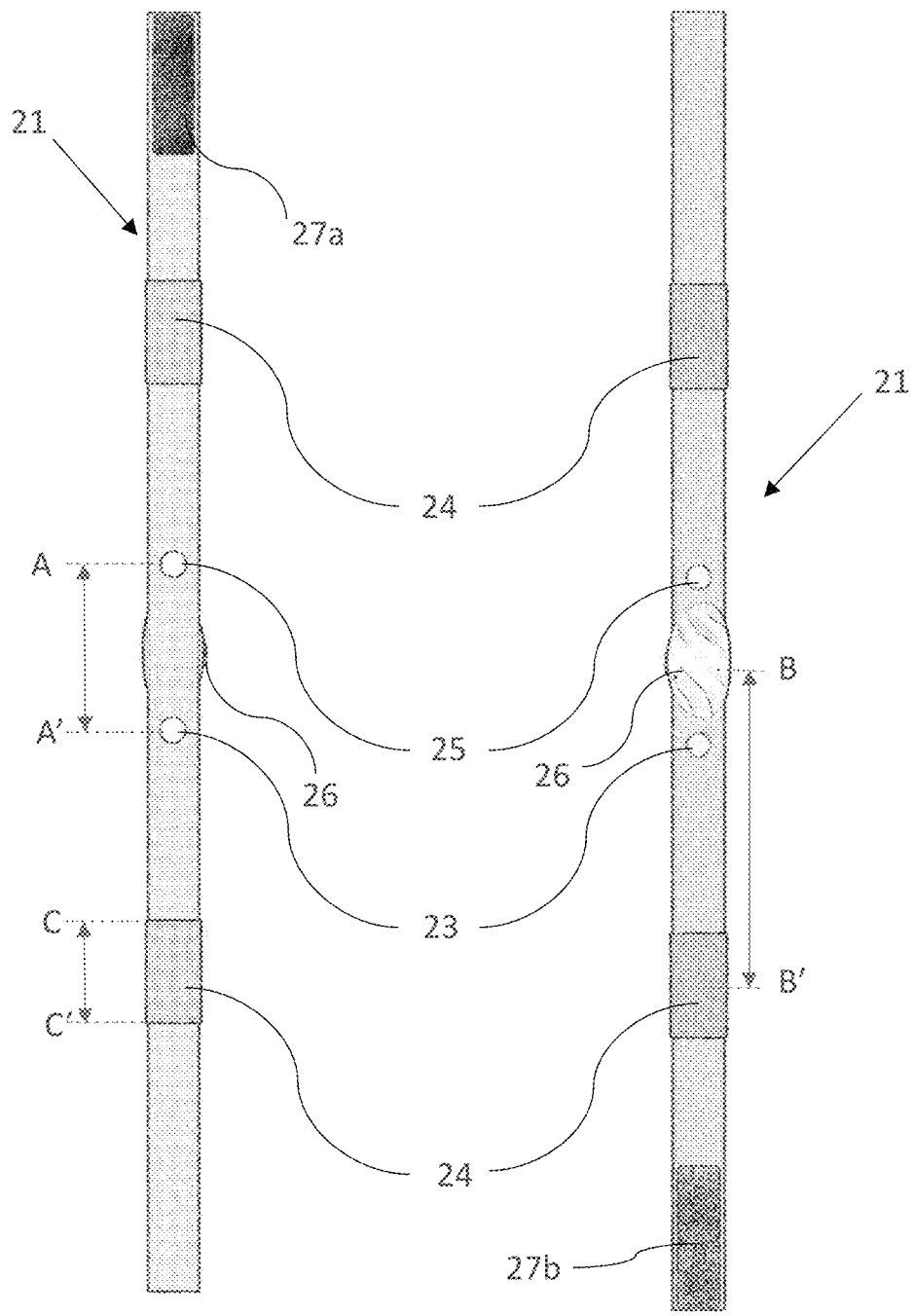

As shown in FIG. 1A, which is a perspective view, the bioelectrical signal acquisition device 20 includes a headband 21, a sensing electrode 23 attached to the headband 21, a grounding electrode 25 attached to the headband 21, two reference electrodes 24 attached to the headband 21, a processing unit 26 attached to the headband 21, and attachment elements 27a and 27b (referring to FIG. 1C).

As shown in FIG. 1B, which is a bottom planform view, and FIG. 1C, which is a top planform view, the bioelectrical signal acquisition device 20 includes a headband 21, a sensing electrode 23, a grounding electrode 25, two reference electrodes 24, a processing unit 26, and attachment elements 27a and 27b. As used here, the bottom planform view shows a side the headband 21 that is in contact with a user's body part (e.g., head) when the bioelectrical signal acquisition device 20 is being worn; and the top planform view shows a side of the headband 21 that is not in contact (or at least not in full contact) with the user's body part when the bioelectrical signal acquisition device 20 is being worn.

Figure 1F:
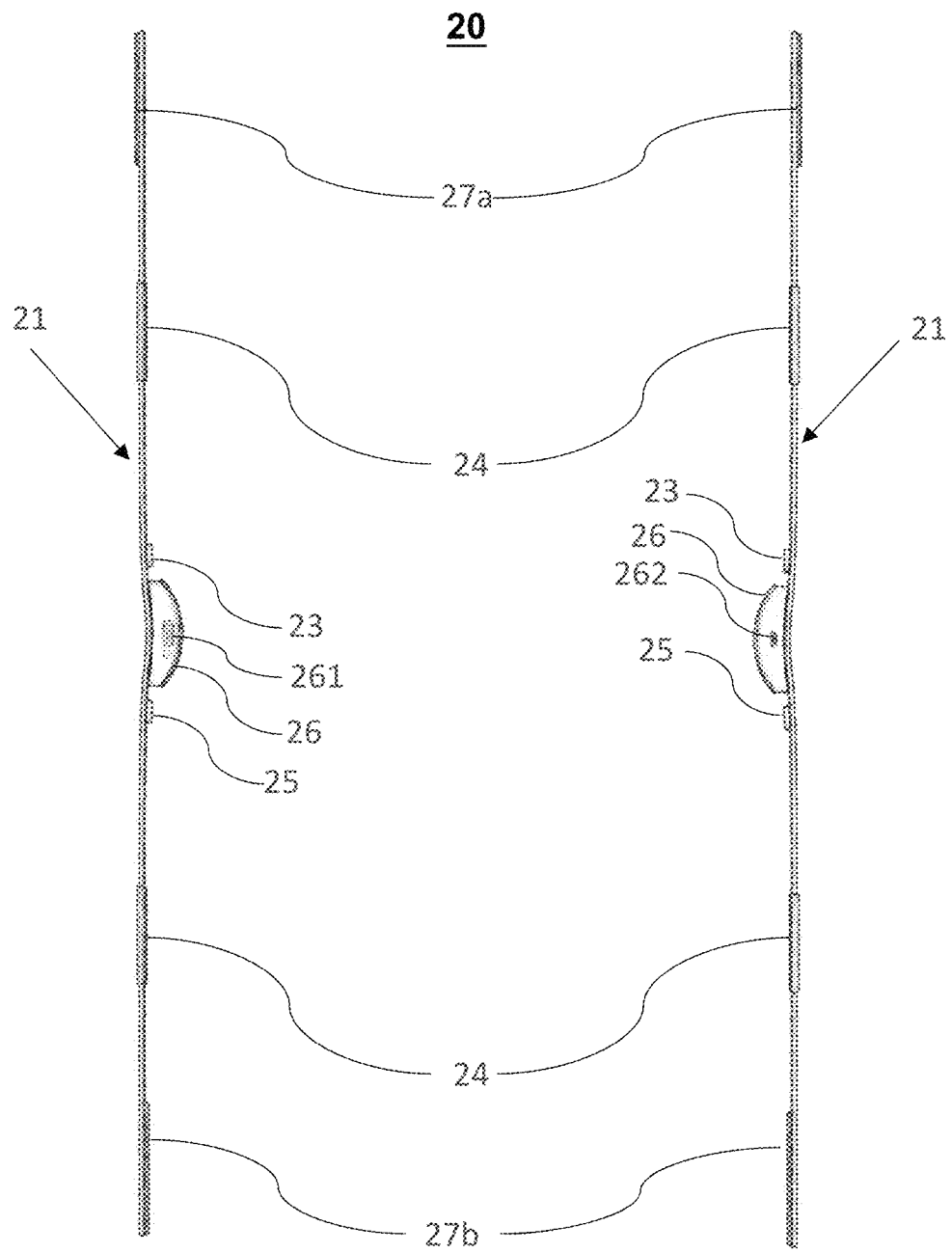
Figure 1F:
Figure 1G:

As supplements to FIGS. 1A, 1B, and 1C, FIGS. 1D-1G are other views of the bioelectrical signal acquisition device 20. In particular, FIG. 1D shows a first side view of the bioelectrical signal acquisition device 20 and FIG. 1E shows a second side view of the bioelectrical signal acquisition device 20. As shown in FIGS. 1D and 1E, the bioelectrical signal acquisition device 20 includes a headband 21, a sensing electrode 23, a grounding electrode 25, two reference electrodes 24, a processing unit 26, and attachment elements 27a and 27b. FIG. 1F shows a first end view of the bioelectrical signal acquisition device 20, and FIG. 1G shows a second end view of the bioelectrical signal acquisition device 20.

Figure 2:
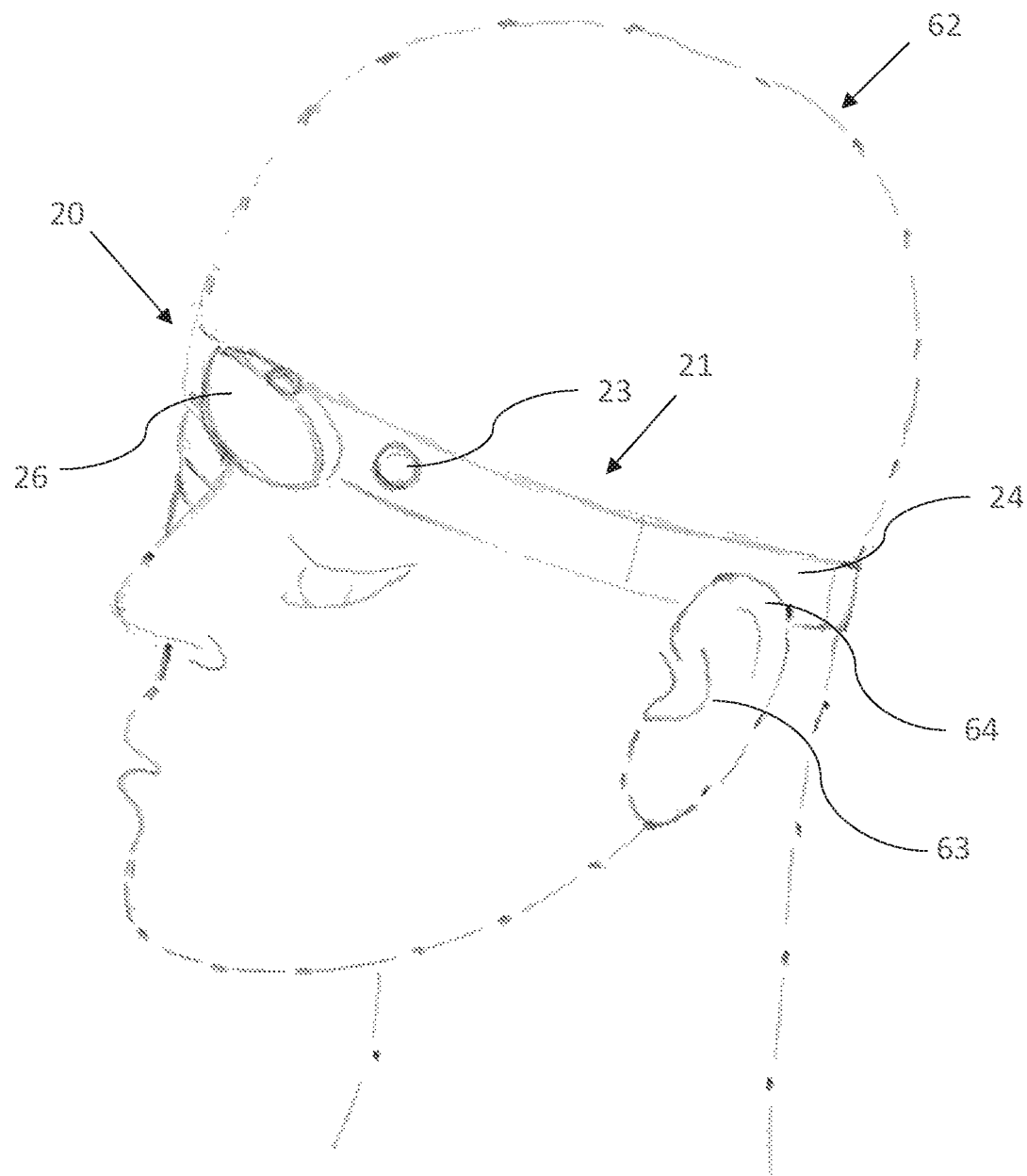
FIG. 2 is a schematic diagram illustrating an exemplary bioelectrical signal acquisition device according to some embodiments of the present disclosure when the device is being worn on a user's head.

FIG. 2 is schematic diagram illustrating an exemplary bioelectrical signal acquisition device 20 according to some embodiments of the present disclosure when the device is being worn by a human user 60 on the user's head 62. In the particular configuration shown in FIG. 2, the bioelectrical signal acquisition device 20 is worn in a manner that the distal ends of the headband 21 are attached to each other, the headband 21 is wrapped around the user's head 62, the sensing electrode 23 contacts the skin on the forehead of the user, the sensing grounding electrode 25 contacts the skin on the forehead of the user (referring to FIG. 4A), and the reference electrode 24 contacts the skin above an ear 63 of the user 60. It should be noted, however, that there are more positioning possibilities for the electrodes, as well as different ways to wear the bioelectrical signal acquisition device 20; and part of the positioning options and various ways of wearing are described and discussed below (e.g., in combination with the illustrations shown in FIGS. 3A-3D).

The various parts of the bioelectrical signal acquisition device 20 serve various functions. However, it should be noted that the embodiment of the bioelectrical signal acquisition device 20 shown in FIGS. 1A-1G and 2 provides only some of the product designs envisioned in the present disclosure. Other alternative product designs, without departing from the descriptions herein provided or general principles of science and engineering, should also be considered part of the present invention.

Referring to FIGS. 1A-1G, the bioelectrical signal acquisition device 20 includes a headband 21 configured to be wearable around a user's head. For a more detailed illustration, refer to FIG. 2. The headband 21 generally refers to a band-shaped flat body to which various electronic elements (e.g., the electrodes, wires, and processing unit) can be attached in different manners. In some embodiments, the headband 21 includes a single piece of band material to which the electronic elements are attached. For example, wires connecting the electrodes and the processing unit can be buried and/or sewed in the headband 21; the electrodes can be integrated into the headband 21. In some embodiments, the headband 21 includes more than one piece of material, whereas the pieces are connected by the electronic elements. For example, in certain embodiments, one or more electrodes (e.g., the reference electrodes 24 or the sensing electrode 23) can connect different pieces of the headband 21 so that other electronic elements may be attached thereto.

The headband 21 may be made from various types of materials. In some embodiments, the headband 21 is made from a soft material, configured to provide comfort when the bioelectrical signal acquisition device 20 is being worn and not disturb the user when the user sleeps or prepares to fall asleep. In some embodiments, the headband 21 is made from an elastic material, configured to provide a balance of flexibility and tightness so that when the bioelectrical signal acquisition device 20 is being worn the user feels comfortable and the bioelectrical signal acquisition device 20 can stay in place when the user sleeps or prepares to fall asleep. The headband 21 may be made with one or more types of materials, including but not limited to: rubber or stretchable synthetic (e.g., spandex) materials, rubber or stretchable synthetic cores that are bound or wrapped in polyester, cotton, nylon, neoprene, or a blend of fiber threads, etc.

Referring to FIGS. 1A-1G and FIG. 2, the bioelectrical signal acquisition device 20 includes a sensing electrode 23 and a reference electrode 24. In some embodiments, the sensing electrode 23 and the reference electrode 24 are configured to receive bioelectrical signals from the user's head. In some embodiments, there may be more than one sensing electrode 23. In some embodiments, there may be more than one reference electrode 24. As parts of a circuit, the sensing electrode(s) 23 and the reference electrode(s) 24 are configured to provide sensing signals from the user's head.

It should be noted that the terms "sensing electrode" and "reference electrode" can be exchanged when referring to particular electrodes. These electrodes both provide inputs that are used in generating the sensing signals. Generally, "sensing electrode" refers to the electrode that is positioned on the headband 21 so that it contacts the skin on the forehead of the user when the user wears the bioelectrical signal acquisition device 20 on the user's head; "reference electrode" refers to the electrode that contacts the skin of the user when the user wears the bioelectrical signal acquisition device 20 on the user's head and forms a circuit with the sensing electrode. However, it should also be noted that the terms may be exchanged, as long as the electrodes serve the same functions as a combination as indicated above.

Referring to FIGS. 1A-1E, the sensing electrode 23 is made from one or more materials that are at least partly conductive. In the embodiment here, the sensing electrode 23 is a metal pin with one or more parts that penetrate the flat body of the headband 21 and can be seen from both the top view (FIG. 1C) and the bottom view (FIG. 1B). For the bottom view (showing the side of the headband 21 contacting the user's head), the sensing electrode 23 is exposed so that it can contact the user's skin when the bioelectrical signal acquisition device 20 is being worn. In certain embodiments, the sensing electrode 23 protrudes from the bottom surface (the surface in contact with the user's head) of the headband 21, for example, for 1-2 mm. In certain preferred embodiments, as shown in FIGS. 1D-1E, the sensing electrode 23 does not visibly protrude from the bottom surface of the headband 21 but is approximately even with the bottom surface. In certain embodiments, the sensing electrode 23 does not visibly protrude from the bottom surface of the headband 21 but sinks slightly (e.g., 0.1-1 mm) into the bottom surface.

It should be noted that there is no specific requirement as to the format of the sensing electrode 23. For example, the sensing electrode 23 can be made from other types of conductive materials (e.g., the materials of the reference electrode 24 as describe below). As another example, while the embodiments shown in FIGS. 1A-1G include one sensing electrode 23, the number of sensing electrodes 23 may be one, two, or more. It is only necessary that the sensing electrode(s) 23 be capable of contacting the user's skin on the forehead when the bioelectrical signal acquisition device 20 is being worn and collecting signals from the user's head.

Referring to FIGS. 1A-1E, the bioelectrical signal acquisition device 20 includes a grounding electrode 25. In some embodiments, the grounding electrode 25 is configured to provide electronic grounding for the sensing signals. In the embodiments here, the grounding electrode 25 is a metal pin with one or more parts that penetrate the flat body of the headband 21 and can be seen from both the top view (FIG. 1C) and the bottom view (FIG. 1B). For the bottom view (showing the side of the headband 21 contacting the user's head), the grounding electrode 25 is exposed so that it can contact the user's skin when the bioelectrical signal acquisition device 20 is being worn. In certain embodiments, the grounding electrode 25 protrudes from the bottom surface (the surface in contact with the user's head) of the headband 21, for example, for 1-2 mm. In certain preferred embodiments, as shown in FIGS. 1D-1E, the grounding electrode 25 does not visibly protrude from the bottom surface of the headband 21 but is approximately even with the bottom surface. In certain embodiments, the grounding electrode 25 does not visibly protrude from the bottom surface of the headband 21 but sinks slightly (e.g., 0.1-1 mm) into the bottom surface.

In some embodiments, the grounding electrode 25 is positioned on the headband to contact the user's skin when the user wears the bioelectrical signal acquisition device 20 on the user's head. In some embodiments, the sensing electrode 23 and the grounding electrode 25 are positioned symmetrically to a mid-line of the headband 21. In some embodiments, when the bioelectrical signal acquisition device 20 is worn by the user on the user's head, as shown in FIG. 2, the sensing electrode 23 and the grounding electrode 25 are symmetrical of a sagittal plane of the user's body. It should be noted that there is no specific requirement that the grounding electrode 25 be shaped and/or positioned. It is necessary that the grounding electrode 25 be capable of contacting the user's skin when the bioelectrical signal acquisition device 20 is being worn, and that the grounding electrode 25 and the sensing electrode 23 are positioned apart with a sufficient distance for effective grounding. The grounding electrode 25 can be made from other types of conductive materials (e.g., the materials of the reference electrode 24 as describe below). There may also be more than one grounding electrode 25.

Referring to FIGS. 1A-1E, the bioelectrical signal acquisition device 20 includes two reference electrodes 24. However, it should be noted that there may be only one reference electrode 24 and there may be more than two reference electrodes 24 in the bioelectrical signal acquisition device 20. The reference electrode 24 is made from one or more materials that are at least partly conductive. In some embodiments, the reference electrodes 24 may include soft and conductive materials including but not limited to conductive fibric, conductive rubber, conductive silicon, a thin layer of metal sheet, and any combinations thereof. In certain preferred embodiment here, the reference electrodes 24 include conductive fibric.

The reference electrodes 24 are configured and positioned to contact the user's skin when the bioelectrical signal acquisition device 20 is being worn on the user. In certain embodiments, the reference electrode 24 is formatted as a piece of conductive material (e.g., conductive fibric) circularly covering a segment of the headband 21. In certain preferred embodiments, the presence of the reference electrode 24 only adds slightly to the thickness of the headband 21 (the illustrations of FIGS. are not in proportion). In certain embodiments, the reference electrode 24 is made from soft and flexible material to provide comfort to the user.

It should be noted that there is no specific requirement as to the format of the reference electrode 24. For example, in certain embodiments, the reference electrode 24 can be made from other types of conductive materials (e.g., the materials of the sensing electrode 23 as describe above).

Sensing signals are produced by combining signals collected by the sensing electrode 23 and signals collected by the reference electrode 24. Specifically, the DC electric potential differences, or voltage, between the sensing electrode 23 and the reference electrode 24, is measured multiple times (e.g., several hundred times) per second. Depending on the positioning of the electrodes, the user's physiological conditions (e.g., awake, sleep onset, or asleep), the sensing signals may include various types of signals. For example, in some embodiments, the sensing signals include electroencephalogram (EEG), electromyogram (EMG), and/or Electrooculography (EOG) signals of the user. In some embodiments, the sensing signals include primarily EEG signals. In some embodiments, the sensing signals include primarily EEG and EOG signals.

Referring to FIGS. 1A-1G and 2, the bioelectrical signal acquisition device 20 includes a processing unit 26, which is configured to generate digital bioelectrical signals based on the sensing signals. In some embodiments, the processing unit 26 includes an electrical signal amplification circuit configured to amplify the sensing signals. In some embodiments, the processing unit 26 includes an analog-to-digital converting circuit configured to convert analog signals to digital signals. Specific connections between the electrodes and the processing unit 26 may vary. The bioelectrical signal acquisition device 20 may include signal wires connecting the sensing electrode 23 and the reference electrodes 24 to an input port of the signal amplification circuit of the processing unit 26. In some embodiments, at least a portion of the wires are shielded wires comprising a shielding layer, and the shielding layer is connected to the grounding electrode Besides signal conversion and processing, the processing unit 26 may perform other functions. For example, the processing unit 26 may include a transmission element configured to transmit signals to other devices or units (e.g., a computational unit), via wired or wireless transmission (e.g., WIFI or BLUETOOTH). In certain embodiments, the transmission element is physically integrated into the processing unit 26. In certain embodiments, the transmission element is a separate structure from the processing unit 26. In some embodiments, the processing unit 26 may also be configured receive incoming data and integrate the incoming data with the sensing signals or the digital bioelectrical signals.

Referring to FIGS. 1A-1G and 2, the bioelectrical signal acquisition device 20 includes connecting elements 27a and 27b, which are configured to connect two distal ends of the headband 21 to form a circle. In some embodiments, the connecting elements 27a and 27b are configured to be capable of adjusting the circumference of the circle so that the bioelectrical signal acquisition device 20 can be properly wrapped around a user's head. Here, "properly wrapped" means a balance of comfort (to reduce disturbance to the user) and tightness (to ensure effective signal collection in a long period of time). The connecting elements of 27a and 27b can be any format or materials, such as but not limited to hook-and-loop fasteners, snap buckle straps, and spaced button pairs. It should also be noted that The distances between the electrodes and the size of the electrodes may vary. Referring to FIGS. 1B and 1C, in some embodiments, the distance between the centers of the grounding electrode 25 and the sensing electrode 23, marked as AA', may be in a range of 5-30 cm; in certain embodiments, AA' may be in a range of 5-10 cm; in certain embodiments, AA' may be in a range of 7-10 cm; In certain embodiments, AA' may be in a range of 7-8 cm. Referring to FIGS. 1B and 1C, in some embodiments, the distance between a center line of the headband 21 and the center of the reference electrode 24, marked as BB', may be in a range of 5-30 cm; in certain embodiments, BB' may be in a range of 10-25 cm; in certain embodiments, BB' may be in a range of 12-20 cm; in certain embodiments, BB' may be in a range of 15-18 cm, in certain embodiments, BB' may be in a range of 16-17 cm. Referring to FIGS. 1B and 1C, in some embodiments, the length of the reference electrode 24 along the length of the headband 21, marked as CC', may be in a range of 1-10 cm; in certain embodiments, CC' may be in a range of 2-8 cm; in certain embodiments, CC' may be in a range of 4-6 cm; in certain embodiments, CC' may be around 5 cm. In some embodiments, a larger (e.g., longer in the longitudinal direction of the headband 21) reference electrode 24 may allow for more flexible arrangement for the user to choose how to wear the bioelectrical signal acquisition device 20. However, this possible benefit needs to be balanced with cost of material and effectiveness of signal collection.

As shown in FIGS. 1A, 1D, 1E and 2, the processing unit 26 may include a power switch 261 and a charging port 262. In some embodiments, the power switch 261 is configured to control on/off state of the processing unit 26, as well as on/off state of certain functions of the processing unit 26, such as but not limited to signal transmission. In some embodiments, the charging port 262 is configured to be used to charge the processing unit 26. In certain embodiments, the charging port 262 may also be configured to send data to or receive data from other devices or units.

Referring to FIGS. 1A-1G and 2, the bioelectrical signal acquisition device 20 may be configured to produce digital bioelectrical signals of a user when the user sleeps or prepares to fall asleep. In some embodiments, the headband 21 is made from soft and elastic material and configured to not disturb the user when the user sleeps or prepares to fall asleep. In some embodiments, the signal wires are integrated in the headband 21 and configured to not disturb the user when the user sleeps or prepares to fall asleep. In some embodiments, the electrodes are structured and positioned to not the user when the user sleeps or prepares to fall asleep. In some embodiments, the digital bioelectrical signals comprise electroencephalogram (EEG), electromyogram (EMG), and/or Electrooculography (EOG) signals of the user when the user sleeps or prepares to fall asleep. In some embodiments, the digital bioelectrical signals comprise primarily EEG signals of the user when the user sleeps or prepares to fall asleep. In some embodiments, the digital bioelectrical signals comprise EEG and EOG signals of the user when the user sleeps or prepares to fall asleep.

FIG. 3A-3D are diagrams illustrating positioning of the reference electrode around a user's ear according to some embodiments of the present disclosure. FIG. 3A shows a side view of a user's ear 63 when the reference electrode 24 is positioned above the user's ear 63. FIG. 3B shows a sectional view of the user's ear 63 and head when the reference electrode 24 is being positioned above a user's ear 63.

As shown in FIGS. 2, 3A, and 3B, in certain embodiments, one of the possible position combinations of the electrodes when the bioelectrical signal acquisition device 20 is being worn is that the sensing electrode 23 is contacting the skin on the forehead of the user's head 62, and the reference electrodes 24 are contacting the skin above the ear 63 of the user's head 62. In particular, referring to FIGS. 3A and 3B, the reference electrode 24 is positioned, at least in part, behind a top part of the ear helix 64. In other words, the reference electrode 24 is partly positioned between the top part of the ear helix 64 and the head of the user. The style shown in FIGS. 2, 3A, and 3B, with minor modifications (e.g., slightly highly or lower) is the most common style for wearing any headband-type device.

FIG. 3C shows a sectional view of the reference electrode 24 and the headband 21 at the location marked as DD' in FIG. 3A. FIG. 3C demonstrates that the headband 21 is covered by the reference electrode 24, which is connected to a wire 81. It should be noted that FIG. 3C is not in proportion. For clarity purposes, the space between the headband 21 and the reference electrode 24 is exaggerated.

As shown in FIG. 3C, with a rough division as shown with dotted lines, the headband 21 has a bottom side 211, defined as the side facing the user's head 62 when the user wears the bioelectrical signal acquisition device 20, and a top side 212, defined as side facing away from the user's head 62 when the user wears the bioelectrical signal acquisition device 20; between the bottom side 211 and the top side 212 is an upper edge 214, which points up when the user stays upright, and a lower edge 213, which points down, when the user wears the bioelectrical signal acquisition device 20. As shown in FIG. 3C, with the rough division as shown with dotted lines, the bottom side 211 can be divided into an upper portion 211a, a middle portion 211b, and a lower portion 211c; similarly, the top side 212 can be divided into an upper portion 212a, a middle portion 212b, and a lower portion 212c.

As a general design, in some embodiments, the sensing electrode 23 is positioned on the headband 21 to contact the skin on the forehead of the user, and the reference electrode 24 is positioned on the headband to contact the skin on, over, above, behind, or around an ear of the user, when the user wears the bioelectrical signal acquisition device 20 on the user's head. In addition, as indicated above, the terms reference electrode 24 and sensing electrode 23 can be exchanged. Therefore, in some embodiments, the sensing electrode 23 is positioned on the headband 21 to contact the skin on, over, above, behind, or around an ear of the user, and the reference electrode 24 is positioned on the headband 21 to contact the skin on the forehead of the user, when the user wears the bioelectrical signal acquisition device on 20 the user's head. Therefore, the descriptions herein provided for the sensing electrode 23 and the reference electrode 24 can also be exchanged.

In some embodiments, referring to FIG. 3A, the user has hair 66 above the user's ear 63. The hair 66 in some cases would be an obstacle that may block the reference electrode 24 from properly contacting the user's skin, making signal collection more difficult. However, as long as part of the reference electrode 24 can contact a sufficient area of the user's skin, even if the other part of the reference electrode 24 is blocked, signal collection would still be possible. Whether a partial blockade by hair would be problematic depends on the length and thickness of the hair and positioning of the bioelectrical signal acquisition device 20. Since the skin close to the connecting part of the head and the ear is less likely to be covered by hair, certain designs and positioning of the reference electrode 24 aim to minimize the chance of hair blockage. In addition, the designs and positioning of the reference electrode 24 aim to improve the chance of effective signal collection when the bioelectrical signal acquisition device 20 is being worn, not only in the way shown in FIG. 3B, but also in other way, where various ways of wearing the bioelectrical signal acquisition device 20 are accorded different weights due to the likelihood of being used.

In some embodiments, the reference electrode 24 covers at least a lower portion 211c of the bottom side 211 of a segment of the headband 21, thus improving the chance of effective signal collection. In some embodiments, the reference electrode 24 covers at least a lower edge 213 of a segment of the headband 21, thus improving the chance of effective signal collection. In some embodiments, the reference electrode 24 covers at least a lower portion 211c of the bottom side 211 and a lower edge 213 of a segment of the headband 21, thus improving the chance of effective signal collection. In some embodiments, the reference electrode 24 covers at least a middle portion 211b of the bottom side 211, a lower portion 211c of the bottom side 211, and a lower edge 213, of a segment of the headband 21, thus improving the chance of effective signal collection. In some embodiments, the reference electrode 24 covers at least a lower portion 211c of the bottom side 211, a lower portion 212c of the top side 212, and a lower edge 213, of a segment of the headband 21, thus improving the chance of effective signal collection. In some embodiments, the reference electrode 24 covers an entire bottom side 211 and a lower edge 213 of a segment of the headband 21, thus improving the chance of effective signal collection. In some embodiments, the reference electrode 24 encircles a segment of the headband 21, thus improving the chance of effective signal collection.

While it is a common way to wear the bioelectrical signal acquisition device 20 as shown in FIGS. 2, 3A and 3B, there are various other possibilities, one of which is illustrated in FIG. 3D, which shows a side view of a user's ear 63 when the reference electrode 24 is being worn over the user's ear 62. In this style, except for very limited situations, there is no "hair blockade" problem. As long as the reference electrode 24 covers at least part of the bottom side 211 of a segment of the headband 21, the reference electrode 24 can properly contact the skin of the user and collect usable signals. FIG. 3D illustrates the versatility in using the bioelectrical signal acquisition device 20 of the present disclosure. The design and/or positioning the electrodes improve the overall likelihood of monitoring a user's physiological conditions (e.g., sleep) with both comfort and effectiveness for a long period of time.

One of the key difficulties and a long-felt but unsolved need related to wearable electronic devices, especially devices for sleep monitoring, is the balance between comfort and effectiveness. When the wearable device is used for sleep monitoring for a relatively long period of time (e.g., several hours), it needs to be sufficiently comfortable so that it does not disturb the user when the user sleeps or tries to fall asleep. In addition, it also needs to be effective in collecting bioelectrical signals for a long period of time; specifically, the electrodes must properly contact the skin of the user, and the bioelectrical signal acquisition device needs to tight or stable enough when being worn so that it does not fall off or become displaced because falling off or displacement would make signal collection difficult or impossible. The two requirements are somewhat contradictory, but the current disclosure aim to find a balance and satisfy both requirements.

In the present disclosure, certain factors/designs may contribute to the comfort when wearing the device. Such factors/designs include but are not limited to the following: the headband 21 may be made from soft material; the electrodes (e.g., the sensing electrode 23, the grounding electrode 25, and the reference electrodes 24) do not protrude out of the headband 21; some electrodes (e.g., the sensing electrode 23, the grounding electrode 25, and the reference electrodes 24) may be made from soft material (e.g., conductive fibric); the reference electrodes 24 may be made from soft material, such as conductive fibric, waved metal fiber, conductive silicon, conductive rubber or a thin layer of metal sheet; the tightness of the headband 21 can be adjusted; the electrodes are strategically positioned and designed to allow the user to choose his/her own comfortable ways to wear the device from various possibilities (one example being the positioning and design of the reference electrodes 24). It should also be noted that in certain embodiments these factors do not necessarily to be all included to achieve the stated goal.

In the present disclosure, certain factors/designs may contribute to the effectiveness of the bioelectrical signal acquisition device 20 when it is being worn. Such factors/designs include but are not limited to the following: the headband 21 may be made from elastic material, allowing for proper wrapping of the headband 21 around the user's head; proper configuration of the electrodes (e.g., the sensing electrode 23, the grounding electrode 25, and the reference electrodes 24), allowing for effective collection of the sensing signal; the electrodes are strategically positioned and designed to allow for prolonged contact with the user's skin (one example being the position and design of the reference electrode 24). It should also be noted that in certain embodiments these factors do not necessarily to be all included to achieve the stated goal.

Figure 4A:
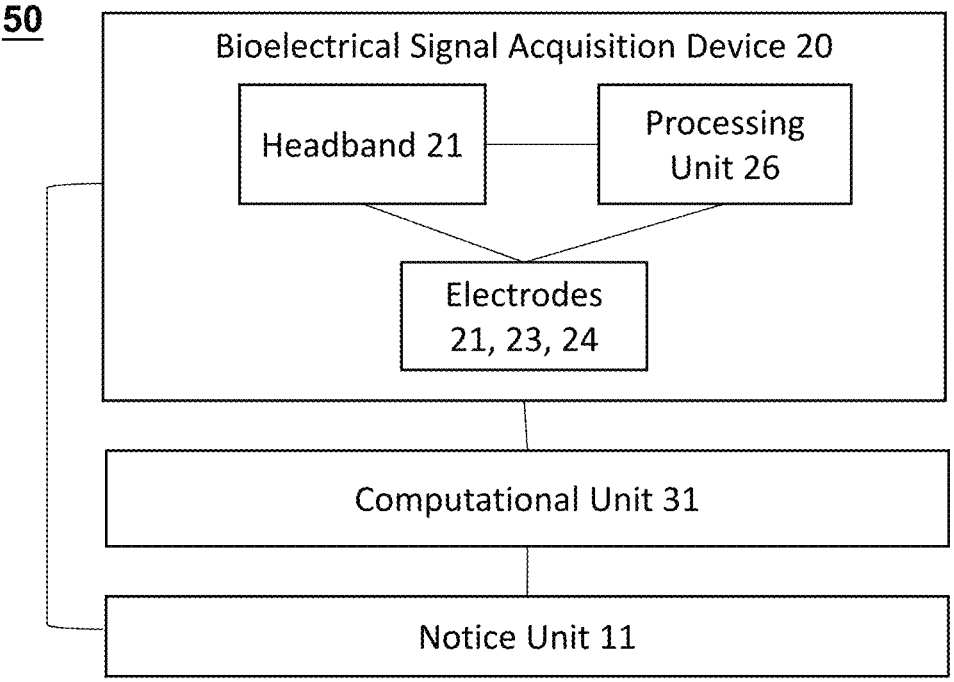
FIGS. 4A-4D are schematic diagrams illustrating an interactive system according to some embodiments of the present disclosure.
Figure 4B:
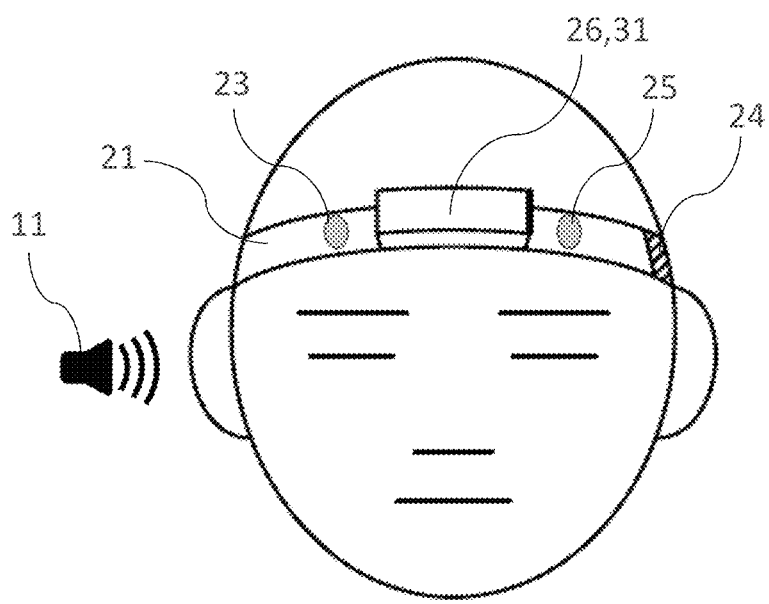
Figure 4C:
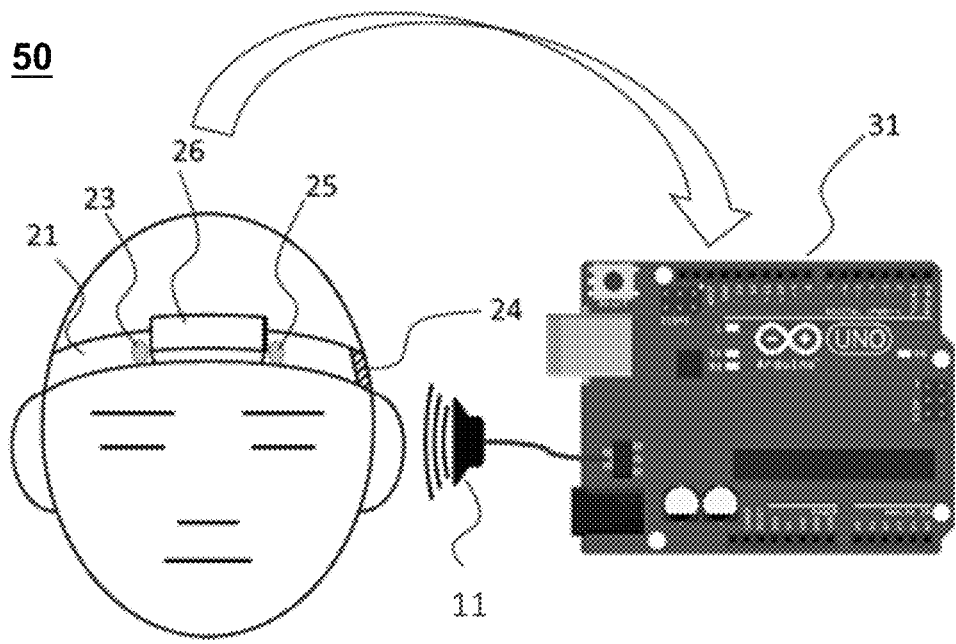
Figure 4D:
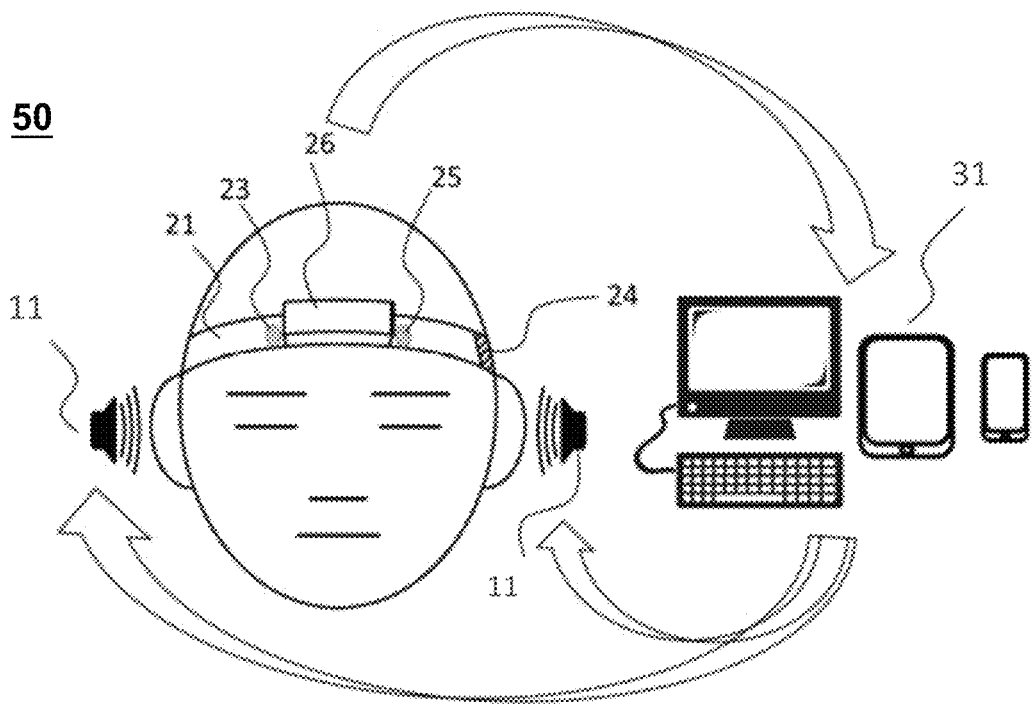

FIGS. 4A-4D are schematic diagrams illustrating an interactive system 50 according to some embodiments of the present disclosure. In some embodiments, the interactive system 50 aims to collect, monitor, process, analyze, and/or transmit bioelectric signals from a subject (e.g., human subject). In some embodiments, the interactive system 50 aims to interact with the subject. In some embodiments, the interactive system 50 aims to influence and/or modulate certain physical or pathological condition of the subject. In some embodiments, the subject is a subject using the bioelectrical signal acquisition device 20. In some embodiments, the interactive system 50 includes the bioelectrical signal acquisition device 20 and the computational unit 31, without the notice unit 11. In certain embodiments, the interactive system 50 include the bioelectrical signal acquisition device 20, the computational unit 31, and the notice unit 11. FIGS. 4B-4D provide examples for the interactive system 50 shown in FIG. 4A.

FIG. 4A is a block diagram showing that the interactive system 50 may include the bioelectrical signal acquisition device 20, a computational unit 31, and a notice unit 11 according to some embodiments of the present disclosure. In some embodiments, the bioelectrical signal acquisition device 20 may include the headband 21, the electrodes (sensing electrode 23, grounding electrode 25, and reference electrode 24), and the processing unit 26, as shown in FIGS. 1A-1G, 2, and 3A-3D.

As shown in FIG. 4A, the interactive system 50 may include a computational unit 31, which may be configured to receive the digital bioelectrical signals from the bioelectrical signal acquisition device 20. The computational unit 31 may be any part, component, processor, board, device, apparatus or system that are have computational and processing capabilities. In some embodiments, the computational unit 31 includes a generic microprocessor. In some embodiments, the computational unit 31 includes a specialized microprocessor. In some embodiments, the computational unit 31 includes part or all of an integrated computing device, such as but not limited to a desk top computer, a laptop computer, a tablet, and a smart phone.

In some embodiments, the computational unit 31 is configured to process and analyze the digital bioelectrical signals provided by the bioelectrical signal acquisition device 20. In some embodiments, the computational unit 31 is configured to generate instructions and/or feedbacks to the bioelectrical signal acquisition device 20 based on predetermined programs. In some embodiments, the computational unit 31 is configured to generate instructions and/or feedbacks to the bioelectrical signal acquisition device 20 based on pre-determined programs and the digital bioelectrical signals provided by the bioelectrical signal acquisition device 20. In some embodiments, the computational unit 31 is configured to generate instructions and/or feedbacks to a notice unit 11 based on pre-determined programs. In some embodiments, the computational unit 31 is configured to generate instructions and/or feedbacks to the notice unit 11 based on pre-determined programs and the digital bioelectrical signals provided by the bioelectrical signal acquisition device 20.

As shown in FIG. 4A, according to some embodiments of the present disclosure, the interactive system 50 may include a notice unit 11, which is configured to facilitate interaction with the subject. For example, the notice unit 11 may be used to send and/or receive signals to and/or from the subject. Such signals may include but be not limited to: visual signals auditory, or sound-based signals; chemical signals (e.g., with perfume or pheromones), and tactile, or touch-based signals, or any combination thereof. In some embodiments, the subject is a human subject using the bioelectrical signal acquisition device 20.

In some embodiments, the notice unit 11 may be configured to receive instructions from the bioelectrical signal acquisition device 20 and/or the computational unit 31 to send signals to the subject. In certain embodiments, the notice unit 11 includes a visual medium (e.g., a screen or a piece of paper) that is configured to present visual signals to the subject. In certain embodiments, the notice unit 11 includes a tactile device that can send touch-based signals (e.g., vibration) to the user. In certain embodiments, the notice unit 11 includes an audio device (in such cases the notice unit 11 may be considered an audio unit) configured to send audio signals (i.e., play audio) to the subject.

In some embodiments, the notice unit 11 may be configured to receive signals from the subject. For example, the notice unit 11 may receive audio signals (or other types of signals) directly from the user when the user speaks or make other types of sound. In some embodiments, the notice unit 11 does not receive signals directly from the subject, but only receive instructions from the computational unit 31, which processes signals from user, such as but limited to the digital bioelectrical signals collected by the bioelectrical signal acquisition device 20 from the subject (user of the bioelectrical signal acquisition device 20).

In some embodiments, the bioelectrical signal acquisition device 20, the computational unit 31, and the notice unit 11 are physically separate devices. For example, the computational unit 31 can be a desk computer, the notice unit 11 can be one or more speakers, and the bioelectrical signal acquisition device 20 can be a separate device as shown in FIGS. 1A-1G. In some embodiments, the bioelectrical signal acquisition device 20 and the computational unit 31 are integrated together, while the notice unit 11 is a physically separate device. For example, the computational unit 31 can be a microprocessor integrated into the bioelectrical signal acquisition device 20, e.g., combined with the processing unit 26 of the bioelectrical signal acquisition device 20. In some embodiments, the computational unit 31 and the notice unit 11 are integrated together, while the bioelectrical signal acquisition device 20 is a physically separate device. For example, the computational unit 31 can be a small phone or tablet, and the notice unit 11 may be the audio and/or display part of the smart phone or tablet, and the bioelectrical signal acquisition device 20 can be a separate device as shown in FIGS. 1A-1G. In some embodiments, the bioelectrical signal acquisition device 20 and the notice unit 11 are integrated together, while the computational unit 31 is a physically separate device. For example, the notice unit 11, as an audio player or tactile device, can be built into the bioelectrical signal acquisition device 20, e.g., together with the reference electrode 24 or the processing unit 26. In some embodiments, the bioelectrical signal acquisition device 20, the computational unit 31, and the notice unit 11 are a single physically integrated device. For example, the computational unit 31 can be microprocessor integrated into the bioelectrical signal acquisition device 20, e.g., combined with the processing unit 26, and the notice unit 11, as an audio player or tactile device, can be integrated into the headband 21 close to or within the reference electrode 24.

The bioelectrical signal acquisition device 20, the computational unit 31, and the notice unit 11 can communicate with or without wire. For example, the bioelectrical signal acquisition device 20 can transmit signals to the computational unit 31 through wire or wirelessly, e.g., with WIFI or BLUETOOTH. As another example, the computational unit 31 can transmit instructions to the notice unit 11 through wire or wirelessly, e.g., with WIFI or BLUETOOTH.

FIG. 4B is a diagram showing in the interactive system 50 according to certain embodiments of the present disclosure, where the computational unit 31 and the bioelectrical signal acquisition device 20 are integrated. As shown in FIG. 4B, in certain embodiments, the bioelectrical signal acquisition device 20 may be a single-channel device (e.g., a single-channel EEG device), the computational unit 31 may be a microcontroller, and the notice unit 11 may be one or more wired audio earplugs connected to the microcontroller by cable. In certain embodiments, the bioelectrical signal acquisition device 20 and the computational unit 31 (microcontroller) are integrated in the same physical structure. It should be noted, as indicated above, that the computational unit 31 and/or the bioelectrical signal acquisition device 20 can be connected to the notice unit 11 wirelessly, e.g., through WIFI or BLUETOOTH.

FIG. 4C is a diagram showing that in the interactive system according to certain embodiments of the present disclosure, where the computational unit 31 is a generic microcontroller. As shown in FIG. 4C, in certain embodiments, the bioelectrical signal acquisition device 20 may be a single-channel device (e.g., a single-channel EEG device), the computational unit may be a generic microcontroller, such as but not limited to an "ARDUINO UNO", and the notice unit 11 may be one or more wired audio speakers connected to the microcontroller by cable. In certain embodiments, the bioelectrical signal acquisition device 20 and the computational unit 31 (microcontroller) are separate physical structures. In certain embodiments, the bioelectrical signal acquisition device 20 also includes a wireless transmitting component that operably communicates with the computational unit 31. In certain embodiments, the wireless transmission is carried out by WIFI or BLUETOOTH. It should be noted, as indicated above, that the computational unit 31 and/or the bioelectrical signal acquisition device 20 can be connected to the notice unit 11 wirelessly, e.g., through WIFI or BLUETOOTH.

FIG. 4D is a diagram showing that in the interactive system according to certain embodiments of the present disclosure, where the computational unit 31 is a separate computing device. As shown in FIG. 4D, in certain embodiments, the bioelectrical signal acquisition device 20 may be a single-channel device (e.g., a single-channel EEG device), the computational unit may be a desktop computer, a laptop computer, a tablet computer, or a smart phone, and the notice unit 11 may be an audio headset connected to the microcontroller wirelessly. In certain embodiments, the bioelectrical signal acquisition device 20 and the computational unit 31 are separate physical structures. In certain embodiments, the bioelectrical signal acquisition device 20 also includes a wireless transmitting component that operably communicates with the computational unit 31. In certain embodiments, the wireless transmission is carried out by WIFI or BLUETOOTH. It should be noted, as indicated above, that the computational unit 31 and/or the bioelectrical signal acquisition device 20 can be connected to the notice unit 11 with wire.

Figure 5A:
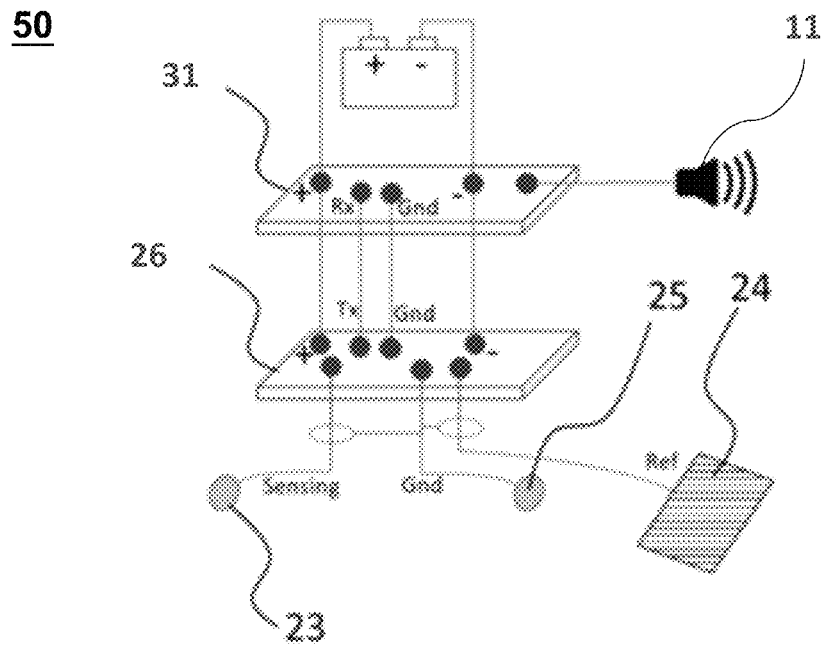
FIGS. 5A-5B are schematic diagrams illustrating the interactive system and the bioelectrical signal acquisition device in more detail according to some embodiments of the present disclosure.
Figure 5B:
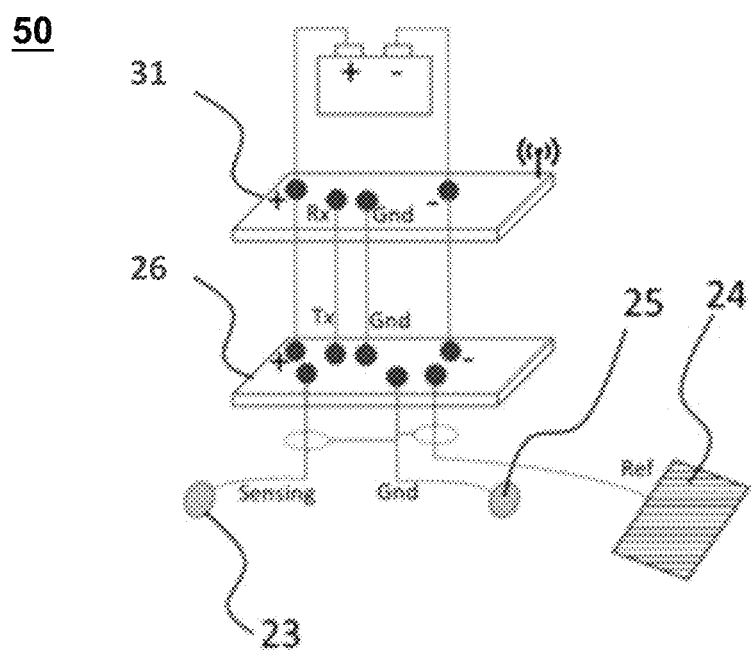

FIGS. 5A-5B are schematic diagrams illustrating the interactive system 50 and the bioelectrical signal acquisition device 20 in more detail according to some embodiments of the present disclosure, where the computational unit 31 and the bioelectrical signal acquisition device 20 are integrated.

FIG. 5A shows simplified and basic wiring of an interactive system 50 including wired connection with the notice unit 11. As shown in FIG. 5A, the bioelectrical signal acquisition device 20 includes a sensing electrode 23, a reference electrode 24, a grounding electrode 25, a processing unit 26, all attached to a headband 21. In certain embodiments, the processing unit 26 includes a processing board as shown in FIG. 5A. In certain embodiments, the bioelectrical signal acquisition device 20 may be a single-channel device, the computational unit 31 may be a microcontroller, and the notice unit 11 may be one or more wired audio earplugs connected to the microcontroller by cable. In certain embodiments, the bioelectrical signal acquisition device 20 and the computational unit 31 (microcontroller) are integrated in the same physical structure. All electrodes are connected to the processing unit 26 by electrical wires. In certain embodiments, the electrical wires for the sensing electrode 23 and reference electrode 24 are shielded wires with the shielding layers, which share direct connection with the grounding electrode. The computational unit 31 is a microcontroller board, which may receive digital bioelectrical signals from the processing unit 26 and execute a set of pre-programed logic combinations, including controlling the notice unit 11, which is an audio unit here, to play a set of pre-recorded sounds.

FIG. 5B shows simplified and basic wiring of an interactive system 50 including wireless connection with the notice unit 11. As shown in FIG. 5B, the bioelectrical signal acquisition device 20 includes a sensing electrode 23, a reference electrode 24, a grounding electrode 25, a processing unit 26, all attached to a headband 21. In certain embodiments, the processing unit 26 includes a processing board as shown in FIG. 5B. In certain embodiments, the bioelectrical signal acquisition device 20 may be a single-channel device, the computational unit 31 may be a microcontroller, and the notice unit 11 may be one or more wired audio earplugs connected to the microcontroller by cable. In certain embodiments, the bioelectrical signal acquisition device 20 and the computational unit 31 (microcontroller) are integrated in the same physical structure. All electrodes are connected to the processing unit 26 by electrical wires. In certain embodiments, the electrical wires for the sensing electrode 23 and reference electrode 24 are shielded wires with the shielding layers, which share direct connection with the grounding electrode. In some embodiments, the computational unit 31 may include a wireless transmission component. In certain embodiments, the computational unit 31 may receive digital bioelectrical signals from the processing unit 26, execute a set of pre-programed logic combinations, and send instructions wirelessly to the notice unit 11, which is an audio unit here, to play a set of pre-recorded sounds.

Referring to FIGS. 4A-4D and 5A-5B, the interactive system 50 may include a bioelectrical signal acquisition device 20, which in some embodiments may be the bioelectrical signal acquisition device 20 shown in FIGS. 1A-1G, 2 and 3A-3D. the interactive system 50 may include a computational unit 31 configured to receive the digital bioelectrical signals from the bioelectrical signal acquisition device 20, process the digital bioelectrical signals and execute one or more logic sets based on the digital bioelectrical signals. Here, the phrase "logic set" (or "logic combination") refers to any action/inaction and/or command that can be taken or generated by pre-programmed instructions. All the actions/inactions and/or commands are presented, stored transmitted, received, obtained, and/or encoded in electronic and/or magnetic signals.

In some embodiments, the computational unit 31, for example, may include COM ports connected to and from a network connected thereto to facilitate data communications. The computational unit 31 may also include a processor (e.g., the microprocessor shown in FIGS. 5A-5B), in the form of one or more processors (e.g., logic circuits), for executing program instructions. For example, the processor may include interface circuits and processing circuits therein. The interface circuits may be configured to receive electronic signals from a bus, wherein the electronic signals encode structured data and/or instructions for the processing circuits to process. The processing circuits may conduct logic calculations, and then determine a conclusion, a result, and/or an instruction encoded as electronic signals. Then the interface circuits may send out the electronic signals from the processing circuits via the bus.

The exemplary computational unit may further include program storage and data storage of different forms including, for example, a disk, and a read-only memory (ROM), or a random-access memory (RAM), for various data files to be processed and/or transmitted by the computational unit. The exemplary computational device may also include program instructions stored in the ROM, RAM, and/or another type of non-transitory storage medium to be executed by the processor. The methods and/or processes of the present disclosure may be implemented as the program instructions. The computational unit 31 may also include an I/O component, supporting input/output between the computer and other components. The computational unit 31 may also send and receive programming and data via network communications.

Merely for illustration, only one microprocessor is illustrated in FIGS. 5A-5B. Multiple processors are also contemplated; thus, operations and/or method steps performed by one processor as described in the present disclosure may also be jointly or separately performed by the multiple processors. For example, if in the present disclosure the processor of the computational unit 31 executes both step A and step B, it should be understood that step A and step B may also be performed by two different processors jointly or separately in the computational unit 31 (e.g., a first processor executes step A and a second processor executes step B or the first and second processors jointly execute steps A and B).

In some embodiments, the interactive system 50 may be configured to monitor sleep patterns of the user when the user sleeps or prepares to fall asleep. In certain embodiments, the interactive system 50 may be configured to monitor existence and pattern of ocular event-related potentials (o-ERPs) when the user sleeps or prepares to fall asleep.

In some embodiments, the interactive system may be configured to monitor eye blink, eye movement, or eyelid squeezing by processing the digital bioelectrical signals.

In some embodiments, for the interactive system 50 of the present disclosure, the computational unit 31 may be a personal computer, a tablet computer, a smart phone, a generic microprocessor, or a specialized microprocessor. In some embodiments, the computational unit 31 may further comprise a low-pass filter, a high-pass filter, or a band-pass filter, or a combination thereof, configured to conduct a digital filtering process on the digital bioelectrical signals provided by the bioelectrical signal acquisition device 20.

As shown in FIGS. 4A-4D and 5A-5B, the interactive system 50 may further include a notice unit 11, which in some embodiments is an audio unit, which is configured to provide audio signals to the user. In certain embodiments, the audio unit may include an audio earplug, a pair of audio-earplugs, a headset, or a speaker. In some embodiments, the audio unit is operationally connected to the computational unit 31 and provides audio signals under control of the computational unit 31.

In some embodiments, the present disclosure also relates to a method of monitoring a physiological or pathological condition of a user, using the interactive system 50 as shown in FIGS. 4A-4D and 5A-5B and herein described, the bioelectrical signal acquisition device 20 as shown in FIGS. 1A-1G, 2, and 3A-3D and herein described, or any other interactive system and bioelectrical signal acquisition device presented and/or describe elsewhere. In some embodiments, the method relates to monitoring sleep patterns of a user. In some embodiments, the method of monitoring sleep patterns of a user includes: providing an interactive system; collecting digital bioelectrical signals of the user with the bioelectrical signal acquisition device when the user is asleep or in a sleep-related stage; and processing the digital bioelectrical signals with a computational unit to monitor the sleep patterns of the user. Here, the phrase "sleep-related stage" refers to the user's time and conditions that are close to the time and condition of sleeping. In certain embodiments, the user is asleep. In certain embodiments, the user is preparing to fall asleep. In certain embodiments, the user is experiencing different stages of sleeping, including but not limited to stage 1 sleep, stage 2 sleep, stage 3 sleep, and rapid eye movement (REM) sleep. In certain embodiments, the user is in an awake stage (wake up time in the morning) immediately after a period of sleep. In certain embodiments, the user is in an awake stage between two close periods of sleep. In some embodiments, the user goes through a duration that combines sleeping and/or some or all of the stages related to sleep.

In some embodiments, the digital bioelectrical signals include EEG, EOG, or EMG signals, or any combination thereof.

In some embodiments, processing the processing the digital bioelectrical signals includes wave analysis of the time-domain signals and spectrum analysis of the frequency-domain signals includes wave analysis of time-domain signals and spectrum analysis of frequency-domain signals. In some embodiments, the sleep patterns include sleep stage, sleep depth and derived results, including total sleep time, onset latency, wake after sleep onset, and sleep efficiency.

Figure 6A:
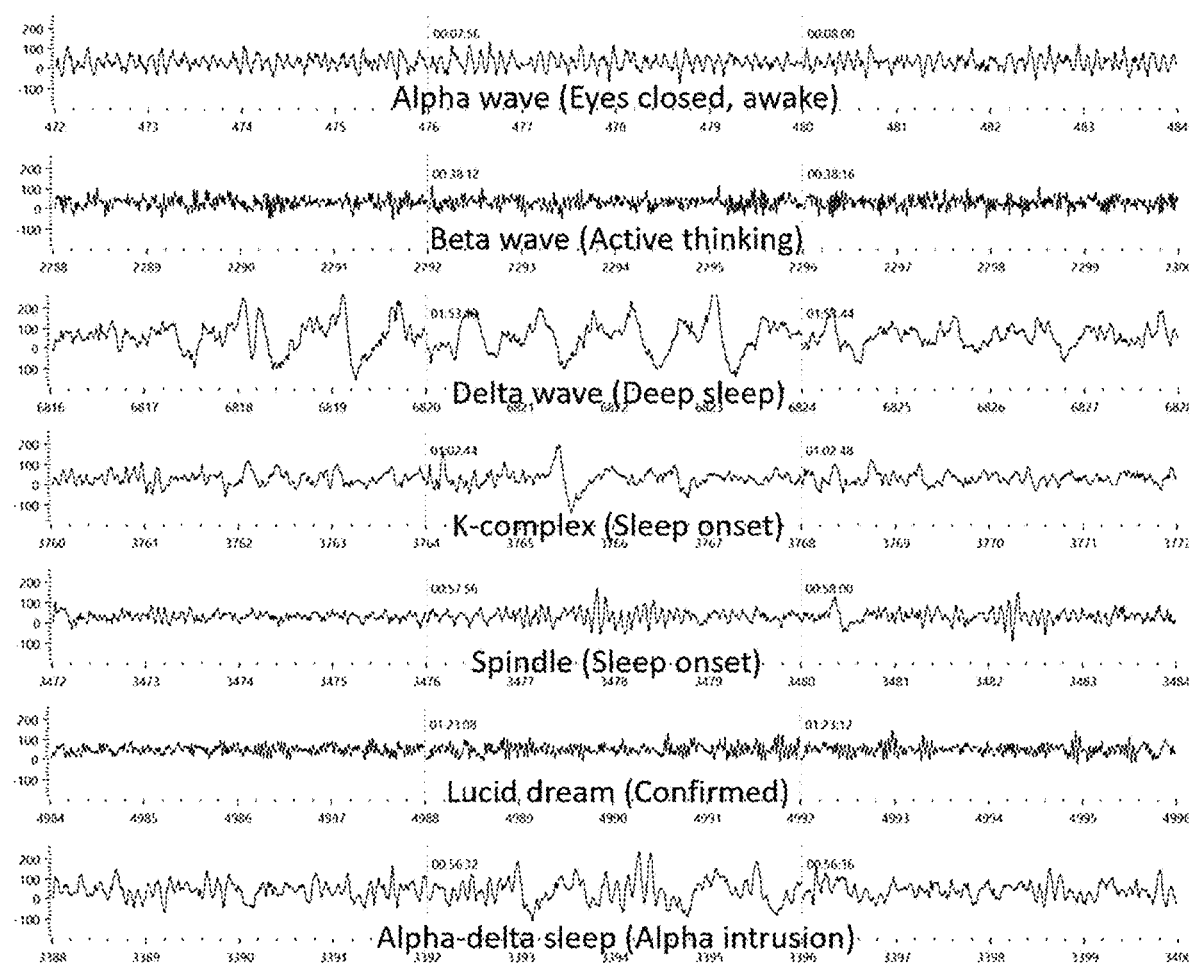
FIGS. 6A-6C show records of digital bioelectrical signals collected from a user's head by the bioelectrical signal acquisition device according to some embodiments of the present disclosure.
Figure 6B:
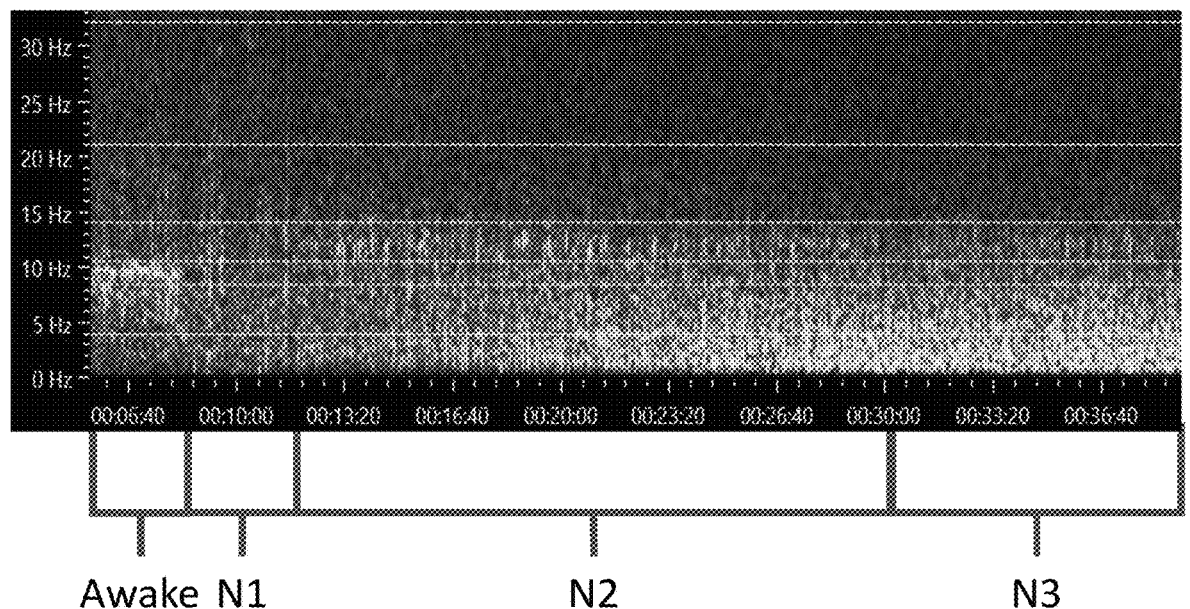
Figure 6C:
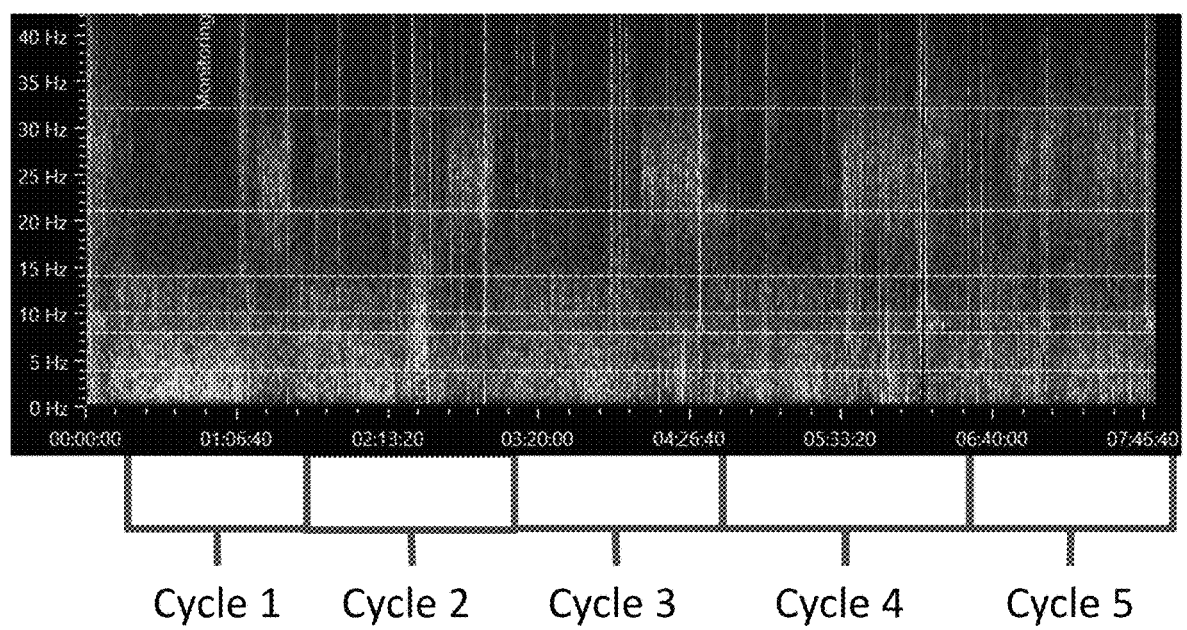

FIGS. 6A-6C show records of digital bioelectrical signals collected from a user's head by the bioelectrical signal acquisition device according to some embodiments of the present disclosure.

FIG. 6A show various types of brainwave data acquired by the bioelectrical signal acquisition device 20 according to some embodiments of the present disclosure. The digital bioelectrical signals, as well as the patterns of signals, are shown in FIG. 6A, and these patterns includes alpha waves (with eyes closed, but user is awake), beta waves (user is engaged in active thinking), delta wave (user is in deep sleep), K-complex pattern (user is in sleep onset stage), spindle pattern (user is in sleep onset stage), lucid dream pattern, and alpha-delta sleep pattern. The patterns shown in FIG. 6A include signature brainwaves for normal health brain states, such as awake, deep sleep, sleep onset, as well as abnormal states, such as lucid dream and alpha-delta sleep. The data shown in FIG. 6A demonstrate the sensitivity, specificity, reliability, and versatility of the bioelectrical signal acquisition device 20 and the interactive system 50 of the present disclosure.

FIG. 6B shows a frequency-domain recording of a user before, during, and after the sleep onset process by the bioelectrical signal acquisition device 20 according to some embodiments of the present disclosure. In essence, FIG. 6B illustrates a typical sleep onset process with excellent data quality acquired by the bioelectrical signal acquisition device 20. With the progress of time:

In the beginning, in the "awake" stage, alpha band (around 10 Hz) is present, indicating that the user of the bioelectrical signal acquisition device the user has closed eyes and relax;

Following the awake stage, alpha band disappears; the user starts to fall asleep (N1 stage, or NREM 1, or S1);

Following the N1 stage, sigma band (11~15 Hz) starts to show up; sigma band represents the spindle wave, which is the signature sleep onset brainwave for the N2 stage (or NREM 2, or S2);

During the N2 stage, low frequency components (0.5~4 Hz), aka delta wave, also starts to get stronger, which indicates that sleep depth is progressing;

The bright Delta band during N3 stage indicates the user is in deep sleep.

The data illustrated in FIG. 6B are highly consistent with classical studies of characteristics of a healthy person's brainwave features during a sleep onset process. Such observations prove that the bioelectrical signal acquisition device of the present disclosure is capable of collecting data with excellent quality. In addition, it shows that the user easily falls asleep, as what has been observed consistently when user wears the bioelectrical signal acquisition device of the present disclosure. Such observations demonstrate that the bioelectrical signal acquisition device is designed to provide comfort and not to disturb the user when the user tries to fall asleep.

FIG. 6C shows a frequency-domain signal presentation of a user during a full night of sleep by the bioelectrical signal acquisition device according to some embodiments of the present disclosure. In essence, FIG. 6C shows continuous (non-stop) recording of a full night sleep of user, after the user has fallen asleep, with excellent data quality. The data demonstrates:

Five natural sleep cycles, approximately 90 minutes each, are clearly observable; each cycle starts with light sleep, progresses to deeper sleep and REM (Rapid Eye Movement) sleep;

The lower frequency component (0.5 to 4 Hz), aka delta waves, indicates the slow-wave sleep; as the night progresses, its strength decreases at the next sleep cycle—this recorded pattern is highly consistent with typical sleep patterns for a healthy human;

The higher frequency component (21 to 32 Hz), aka Beta3 waves, has a strong correlation with REM sleep and dream; as the night progresses, its time length increases at the next sleep cycle—this recorded pattern is highly consistent with typical sleep patterns for a healthy human.

The consistency of the signal patterns here with known patterns is proof that that the bioelectrical signal acquisition device of the present disclosure is capable of collecting data with excellent quality. In addition, it shows that the user sleeps through the night without waking up or being disturbed, as what has been observed consistently when user wears the bioelectrical signal acquisition device of the present disclosure. Such observations demonstrate that the bioelectrical signal acquisition device is designed to provide comfort and stability when the user sleeps or tries to fall asleep. It is observed that even when the user of the bioelectrical signal acquisition device changes positions (e.g., sleeping on the back, or on the side) or makes adjustments (tossing and turning), the bioelectrical signal acquisition device can maintain effective electrode contacts and thus acquire high quality data.

The present disclosure also relates to a method of human-computer interaction. In some embodiments, the method of human-computer interaction is carried out with the assistance of a human-computer interactive system. In some embodiments, the human-computer interactive system includes the interactive system 50 as shown in FIGS. 4A-4D and 5A-5B and herein described. In some embodiments, the human-computer interactive system includes a bioelectrical signal acquisition device. In some embodiments, the human-computer interactive system includes the bioelectrical signal acquisition device 20 as shown in FIGS. 1A-1G, 2, and 3A-3D and herein described. It should be noted, however, that the method of human-computer interaction can be carried out with any other interactive system and/or other bioelectrical signal acquisition device presented and/or describe elsewhere, as long as the system/device is capable of providing certain key functions of the interactive system 50 and the bioelectrical signal acquisition device 20 stated above.

Figure 7:
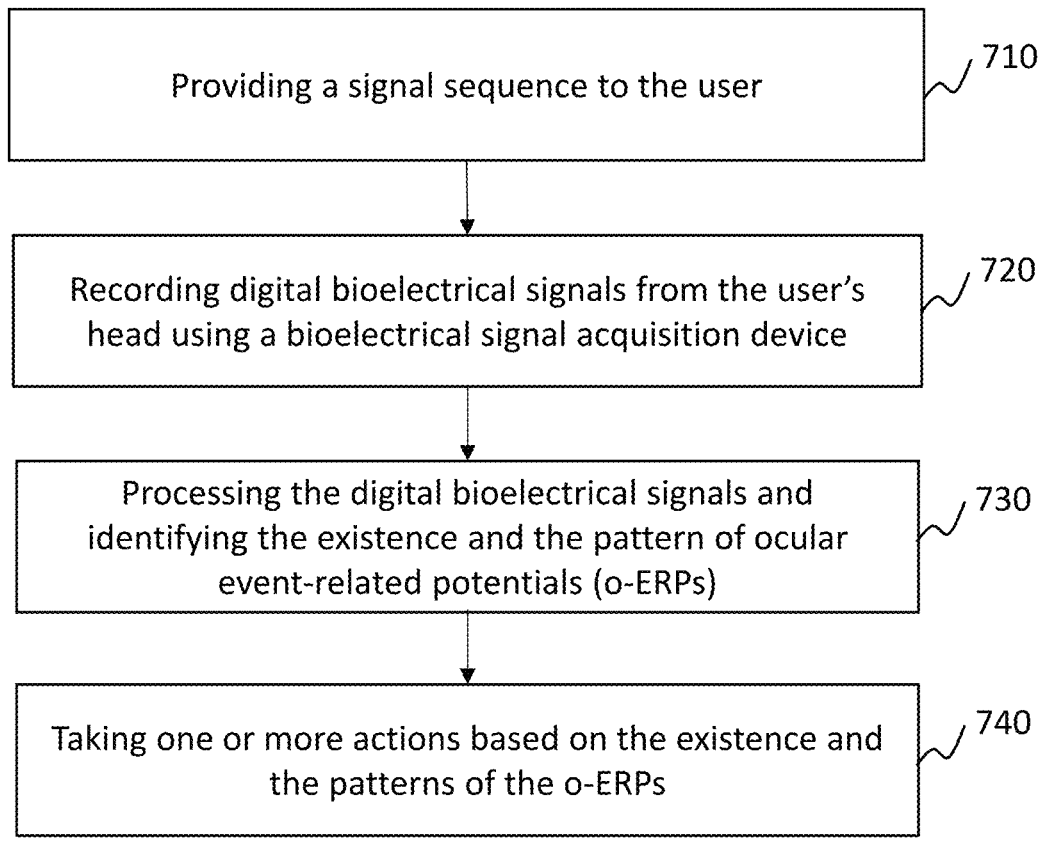
FIG. 7 is a flowchart illustrating an exemplary process for human-computer interaction according to some embodiments of the present disclosure.

Referring to FIG. 7, in some embodiments, the method of human-computer interaction includes: providing a signal sequence to the user; recording digital bioelectrical signals from the user's head using a bioelectrical signal acquisition device; processing the digital bioelectrical signals and identifying the existence and the pattern of ocular event-related potentials (o-ERPs); and taking one or more actions based on the existence and the patterns of the o-ERPs. In some embodiments, the digital bioelectrical signals are processed by an interactive system. In some embodiments, the digital bioelectrical signals are provided by a bioelectrical signal acquisition device. In some embodiments, the digital bioelectrical signals are processed by the computational unit 31 of the interactive system 50. In some embodiments, the digital bioelectrical signals are provided by the bioelectrical signal acquisition device 20.

Referring to 710 of FIG. 7, in some embodiments, the method of human-computer interaction includes a step of providing a signal sequence to the user. The signal sequence can include any signals that may catch the attention of the user or provide notification to the user. The signals can be visual, tactile, verbal, acoustic, olfactory, or any combination thereof. For example, in certain embodiments, the signal sequence includes touching the user, sending vibration to the user, playing sound to the user, or applying light to the user, or any combinations thereof. The signal sequence may include signals with specific properties, patterns, or meanings. The following description would use audio signals according to some exemplary embodiments of the present disclosure. However, it should be noted that sound is only used as examples; other signals, such as but not limited to vibration, can be applied according to the present disclosure, especially by mimicking the signal patterns of the embodiments below based on sound.

In some embodiments, the signal sequence is related to upcoming interactions between the user and the interactive system. In some embodiments, the signal sequence may include more detailed information. For example, the signal sequence may include: a description, a question, or an instruction, or any combination thereof, all relating to upcoming interactions between the user and the interactive system. As used for the signal sequence, "description" includes an explanation of the upcoming interactions, and the explanation is about context, or past, current and expected logic states of the upcoming interactions; "question" includes a presentation of one or more question (e.g., multiple choice questions) with or without possible answers (e.g., list of choices) designed for the upcoming interactions; "instruction" includes information on how to provide a response, such as but not limited to making a selection among the choices presented in the "question". In some embodiments, the description, question, and/or instruction may also serve as a notice to the user that an interaction is about to begin.

In some embodiments, the description, question, and/or instruction may take the form one or more simple and short signals that can be termed as a "notification". In certain embodiments, the notification can indicate to the user that an interaction is about to begin. In some embodiments, the notification may be carried out by one or more simple and short signals. The notification may be based on pre-designed interactions and pre-determined instructions to the user so that the user may know what such a notification entails. For example, a notification can serve as a description, providing all the contents of the description with one or more simple and short signals because the user has been informed beforehand. As another example, a notification can serve as a question or an instruction, providing all the contents of the question or the instruction with one or more simple and short signals because the user has been informed beforehand. In some cases, the signal sequence may only include such a notification.

In some embodiments, the signals sequence is provided by the interactive system 50 as described above. For example, the notice unit 11 can be used to send out the signal sequence. In some embodiments, the notice unit 11 is an audio unit that can send sound signals. In some embodiments, the notice unit 11 can provide tactile signals (e.g., vibration) to the user. For example, the notice unit 11 can be attached to the headband 21 and configured to send vibrating signals to the user when the user wears the bioelectrical signal acquisition device 20.

In some embodiments, the signal sequence may include a signal template (e.g., an audio template) that include repeated or rhythmic signals. For example, the description or instruction may include a signal template. The user can follow pre-determined or real-time explanations and utilize the audio template as basis for input (e.g., by blinking, squeezing eyelid, making eye movement, etc.), thus forming patterns to make a choice or convey certain meanings. In some embodiments, such patterns may take the form of a binary sequence. For example, in certain embodiments, the patterns can be sequences defined in Morse code, since it is a well-known binary sequence representing English alphabets. Certain examples of audio template and corresponding recordings are provided below.

In certain scenarios, especially when there is a high noise level in the data acquired by the bioelectrical signal acquisition device 20, it may be easier (i.e. with higher identification accuracy) to detect input signals (e.g., o-ERPs) with patterns (e.g. following instructions and based on a signal template) than a single input signal.

In some embodiments, the method of human-computer interaction may include a presentation of one or more questions/prompts and list of choices for the upcoming interactions. In some embodiments, the method of human-computer interaction may include a presentation of multiple-choice questions/prompts and list of choices for the upcoming interactions. Such questions/prompts and choices can be presented in various ways, examples of which are shown below.

In some embodiments, the signal sequence may include one or more steps of conditional choices. In some embodiments, one step of the conditional choices may include a binary-choice conditional branch, which is triggered by a presence of a detected o-ERP during a pre-determined time period. In some embodiments, one step of the conditional choices may include a multiple-choice conditional branch, which is triggered by two or more detected o-ERPs during a pre-determined time period.

In some embodiments, the method of human-computer interaction may include eliciting a response from the user. In some embodiments, the method of human-computer interaction may include presenting (e.g. send audio instructions) information to the user on how to provide a response. In some embodiments, the method of human-computer interaction may include presenting (e.g. send audio instructions) information to the user on how to make a selection among the choices presented to the user.

In some embodiments, providing a response includes eye blink, eye movement, or eyelid squeezing, or any combination thereof, by the user.

In some embodiments, the method of human-computer interaction may include providing a plurality of sounds to the user. In some embodiments, the plurality of sounds may include one or more rhythmic audio templates, which may be any kind of audio signals following a pattern and recycling style. In certain embodiments, the rhythmic audio template may include sounds of beats, metronome, ding, chirp, ticking, amplitude-modulated tones or noises, frequency-modulated tones or noises, binaural beats, music pattern, or any form of rhythmic sound. In some embodiments, the user can use the rhythmic audio templates to send responses, such as but not limited to binary signal responses. In some embodiments, for the method of human-computer interaction, the rhythmic audio templates may have a rhythmic frequency between 0.5 Hz and 4 Hz, preferably between 1 Hz and 2 Hz.

Referring to 720 of the process shown in FIG. 7, the method of human-computer interaction may further include recording digital bioelectrical signals from the user's head using a bioelectrical signal acquisition device. In some embodiments, the preferable device the is the bioelectrical signal acquisition device 20 shown in FIGS. 1A-1G, 2, and 3A-3D.

Referring to 730 of the process shown in FIG. 7, the method of human-computer interaction may further include processing the digital bioelectrical signals and identifying the existence and the pattern of ocular event-related potentials (o-ERPs). The processing of the digital bioelectrical signals and the identification of the o-ERPs may be carried out by any device having such capabilities. In some embodiments, the digital bioelectrical signals may be processed by a computing device. In some embodiments, the digital bioelectrical signals may be processed by a computational unit 31 as part of the interactive system 50.

In some embodiments, the method of human-computer inaction may be based on a method of detecting o-ERPs, which comprises operations 720 and 730 of the process shown in FIG. 7.

In some embodiments, the o-ERPs result from eye blinking, eye movement, or eyelid squeezing, or any combination thereof, by the user. In some embodiments, the eye movement and eyelid squeezing are performed by the user with the user's eyes closed.

One of the key difficulties and a long-felt but unsolved need to carry out an effective interaction with a user when the user is trying to sleep, or when the user is in the sleep-onset stage, without disturbing the user to make the user fully awake. The difficulty lies, in large part, in finding a balance between "effectiveness" and "no disturbance". However, sometimes such interactions may be important and/or beneficial and need to be carried out. Some embodiments of the methods of the current disclosure find such a balance so that, at least in some cases, an interaction can be effectively carried out without serious disturbance to the user. In some cases, such balance is achieved by monitoring the o-ERPs, because the actions that trigger the o-ERPs may be minimum. When the user is prepared to fall asleep, the digital bioelectrical signals collected from the user's head are mainly low amplitude EEG signals. With such a background, the o-ERPs can be detected based on a change of signal amplitude, as discussed and shown below. Eye blinks, especially limited (small) blinks, can trigger o-ERPs that can be detected so that further actions can be taken. Eye movements, especially movements when the eyes are closed, can trigger o-ERPs that can be detected so that further actions can be taken. Eyelid squeezing, conducted when the eyes are closed, can trigger o-ERPs that can be detected so that further actions can be taken. While the bioelectrical signal acquisition device 20 and interactive system 50 herein described provide ideal apparatus to fulfill this goal, other devices may also be used if such capabilities are present.

Referring to the method of human-computer inaction and operations 720 and 730 in FIG. 7, the digital bioelectrical signals may have a sample rate ranging from 100 samples per second to 10000 samples per second, preferably from 250 to 1000 samples per second.

Referring to the method of human-computer inaction and operations 720 and 730 in FIG. 7, processing the digital bioelectrical signals and identifying the existence and the pattern of o-ERPs may include a digital filtering process, using a low-pass filter, a high-pass filter, or a band-pass filter, or a combination thereof. In certain embodiments, a filter type is used in the digital filtering process, and the filter type is Butterworth, Chebyshev 1, Chebyshev 2, or Elliptic. In certain embodiments, the low-pass filter has a cut-off frequency that is between 4 Hz and 48 Hz, preferable between 35 and 45 Hz; and the low-pass filter has a number of order that is between 1 and 14, preferable between 8 and 12. In certain embodiments, the low-pass filter is 10th order Butterworth with a cut-off at 40 Hz. the low-pass filter has a lower cut-off frequency between 0.25 Hz and 2 Hz, preferable between 0.5 Hz and 1 Hz. the band-pass filter has an upper frequency limit between 4 Hz and 48 Hz, preferable between 35 Hz and 45 Hz; and the band-pass filter has a lower frequency limit between 0.25 Hz and 2 Hz, preferable between 0.5 Hz and 1 Hz.

Referring to the method of human-computer interaction and operations 720 and 730 in FIG. 7, processing the digital bioelectrical signals and identifying the existence and the pattern of o-ERPs may include analyzing a time-domain presentation, also known as a wave chart, wherein an x-axis represents time, and a y-axis represents the amplitude of an electrical voltage.

Referring to the method of human-computer inaction and operations 720 and 730 in FIG. 7, processing the digital bioelectrical signals may include analyzing a frequency-domain presentation, also known as a spectrogram, wherein an x-axis represents time, and a y-axis represents frequencies. In certain embodiments, identifying the o-ERPs includes setting a proper threshold range (or setting proper thresholds) and identifying patterns in a time-domain presentation that are outside the threshold range. In certain embodiments, the threshold range is from 5 to 300 uV. In certain embodiments, the threshold range is 20 to 100 uV. In some embodiments, identifying the o-ERPs includes template matching with a predefined o-EPR template in the time-domain presentation, with a matching score threshold range from 20 to 90, preferably between 60 to 80. In certain embodiments, identifying the o-ERPs includes detecting long gaps between zero-crosses in the time-domain presentation, wherein the gaps are outside a threshold range. In some embodiments, the threshold range is from 0.01 second to 0.2 second. In certain embodiments, the threshold range is between 0.05 second and 0.15 second.

Referring to the method of human-computer inaction and operations 720 and 730 in FIG. 7, processing the digital bioelectrical signals and identifying the existence and the pattern of o-ERPs may include applying a fast Fourier transform (FFT) to data derived from the digital bioelectrical signals to generate a frequency-domain presentation.

In some embodiments, identifying the o-ERPs is based on a pattern recognition of the o-ERPs based on identifying patterns outside a first threshold range in the time-domain presentation, or identifying patterns outside a second threshold range in the frequency-domain presentation. In some embodiments, identifying the o-ERPs is based on a pattern recognition of the o-ERPs based on identifying patterns outside a first threshold range in the time-domain presentation, and identifying corresponding patterns outside a second threshold range in the frequency-domain presentation.

In some embodiments, pattern recognition of the o-ERPs may include a template matching algorithm, utilizing a template selected from sine waves, triangle wave, rectangle waves, and other periodic waves with the same frequency as the audio's rhythm, enveloped by the binary sequence from the pattern.

Referring to the method of human-computer inaction and operations 720 and 730 in FIG. 7, processing the digital bioelectrical signals and identifying the existence and the pattern of o-ERPs may further include applying a window function to the data derived from the digital bioelectrical signals before the FFT. In certain embodiments, the window function includes rectangular window, triangular window, Parzen window, Welch window, sine window, cosine-sum window, Hann window, Hamming window, Blackman window, or Nattall window, or other common window functions in the field of digital signal processing; preferably a Hann window. In certain embodiments, the window function has a window size ranging between 100 to 100000 samples, preferably collected in N seconds, where N is a positive integer.

Referring to the method of human-computer inaction and operations 720 and 730 in FIG. 7, processing the digital bioelectrical signals and identifying the existence and the pattern of o-ERPs may further include applying a zero-padding step before applying the FFT transformation to raise a number of samples by an $N^{th}$ order of 2, where N is a positive integer.

Referring to the method of human-computer inaction and operations 720 and 730 in FIG. 7, processing the digital bioelectrical signals and identifying the existence and the pattern of o-ERPs may further include applying a step of down sampling before the FFT, reducing the sample rate between 100 and 1000, preferably between 120 and 300.

Referring to the method of human-computer inaction and operations 720 and 730 in FIG. 7, processing the digital bioelectrical signals and identifying the existence and the pattern of o-ERPs may include identifying the o-ERPs is based on a pattern recognition of the o-ERPs based on one or more thresholds in the time-domain presentation, or one or more thresholds in frequency-domain presentation. In some embodiments, the pattern recognition of the o-ERPs includes a template matching algorithm, utilizing a template selected from sine waves, triangle wave, rectangle waves, and other periodic waves with the same frequency as the audio's rhythm, enveloped by the binary sequence from the pattern.

Referring to the method of human-computer inaction and operation 740 in FIG. 7, one or more actions can be taken based on the existence and the patterns of the o-ERPs. The actions can be any actions that can be taken a person or a device. In certain embodiments, the actions are not related directly to the user. In certain embodiments, the actions are directly related to the user. For example, if the envisioned o-ERPs are detected, the interactive system 50 may send another signal sequence to the user and start any iteration of the human-computer interactive process. As another example, if the envisioned o-ERPs are detected, a caregiver (or doctor/nurse) may give the user certain medicine or treatment. In some embodiments, the actions are taken to modulate the physiological, mental, or pathological state of the user. In certain embodiments, the actions may be taken to assist the user's efforts to fall asleep. For example, the interactive system 50 may start playing a soothing music or reading a book to assist the user to fall asleep.

In some embodiments, the one or more actions may include sending another signal sequence to the user. In some embodiments, the one or more actions may include one or more steps of conditional choices. In some embodiments, one step of the conditional choices may include a binary-choice conditional branch, which is triggered by a presence of a detected o-ERP during a pre-determined time period. In some embodiments, one step of the conditional choices may include a multiple-choice conditional branch, which is triggered by two or more detected o-ERPs during a pre-determined time period.

In some embodiments, the one or more actions are taken by the computational unit 31, the audio unit 11, or the bioelectrical signal acquisition device 20.

In some embodiments, the one or more action may include: playing additional sounds with increased or decreased volume, playing a pre-recorded audio file, repeating a previous question, triggering a function menu, starting an insomnia treatment session, starting recording sound, sending a message, or sharing current sleep status in social media, or any combination thereof.

The method of human-computer interaction may further include detecting an abnormal signal before providing the signal sequence to the user. The abnormal signal may be detected by the interactive system 50 or by other devices or a person (e.g., a caregiver). The abnormal signal may be any signal that shows anything that is out of order. For example, the abnormal signal may show that the user is not able to proceed to the sleep onset stage after lying for longer than a threshold period of time.

Certain examples are herein provided based on audio (sound) signals. However, as indicated above, in some cases, the sound signals can be replaced by other signals, such as tactile signals (e.g., vibrations) and convey essentially the same meanings and achieving similar goals. In certain embodiments, the sound signals can be partially replaced, so that other signals (e.g., vibrations) can be combined with the sound signals and achieving similar goals. In some embodiments, providing the signal sequence to the user includes playing a plurality of sounds to the user with an audio unit.

Figure 8A:
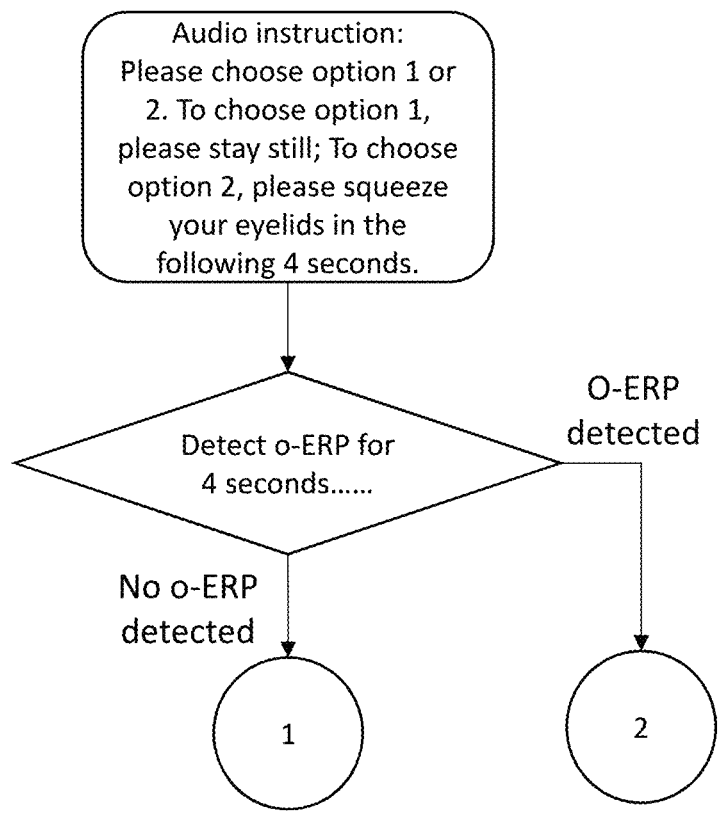
FIGS. 8A-8C show an exemplary process of human-computer interaction and the recorded signals according to some embodiments of the present disclosure.
Figure 8B:
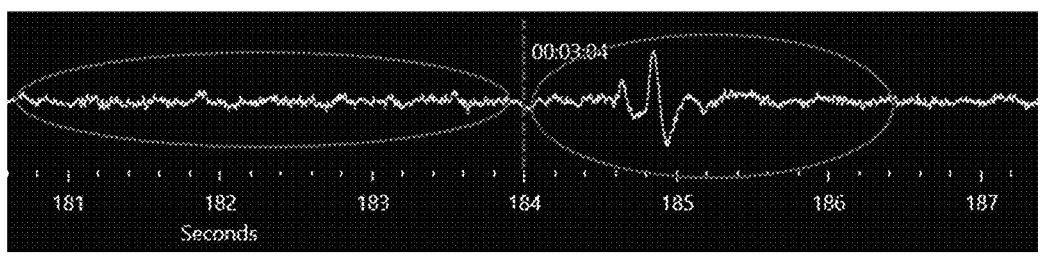
Figure 8C:
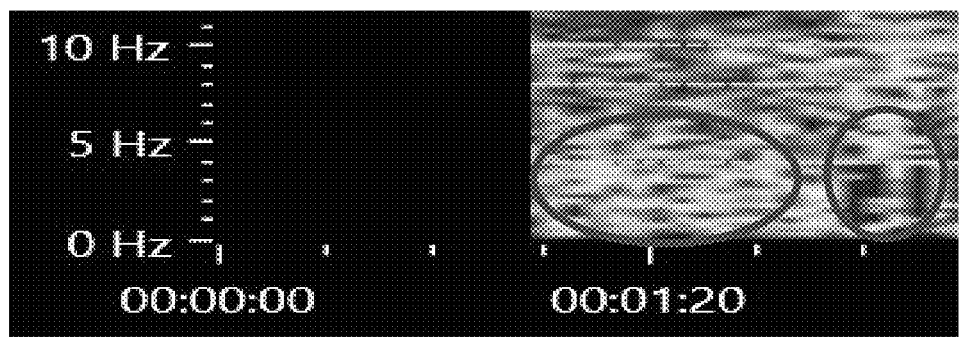

FIGS. 8A-8C show an exemplary process of human-computer interaction and the recorded signals according to some embodiments of the present disclosure. FIG. 8A is a flowchart of the process according to some embodiments of the present disclosure. In some embodiments, the audio unit plays an audio instruction, teaching the user how to make a yes/no selection. Then bioelectrical signal acquisition device 20 collects digital bioelectrical signals from the user and transmits the digital bioelectrical signals to the computational unit 31, where the signals are processed, and o-ERPs are identified and analyzed. Based on the presence of the o-ERP, the choice between yes and no can be made.

FIG. 8B is a time-domain signal presentation, or wave chart, showing some exemplary results of a test that was carried out in the process shown in FIG. 8A. The x axis represents time; they axis represents the amplitude of the electrical voltage difference between the sensing electrode and the reference electrode. As shown in FIG. 8B, the user squeezed his eyelids as instructed and elicited an o-ERP, which was detected by the bioelectrical signal acquisition device 20 and processed by the computational unit 31. As shown in FIG. 8B, when there is no o-ERP (highlighted by the oval on the left), the amplitude variations are low; when there is an o-ERP (highlighted by the oval on the right), the amplitude variations are high. The presence of the o-ERP was determined by setting proper thresholds in the wave chart for amplitude.

FIG. 8C is a frequency-domain presentation, or a spectrogram. The x axis represents time; they axis represents frequency. The color of the pixels represents the calculated values of a fast-Fourier transform (FFT) of the time-domain signals. When there is no o-ERP (highlighted by the oval on the left), the pixels are shown mostly in blue and green; when there is an o-ERP (highlighted by the oval on the right), the pixels are shown mostly in red, orange, and yellow. Another way to describe the frequency-domain presentation is to interpret a warmer color (e.g., yellow, orange, or red) as having higher intensity and a colder color (e.g., green and blue) as having a lower intensity. In fact, in some spectrograms, the intensity is directly represented by brightness of the pixels. Therefore, the presence/pattern of the o-ERPs can be detected by setting proper thresholds in the color (or intensity) in the spectrogram, especially in the low frequency (e.g., less than 5 Hz) range.

Figure 9A:
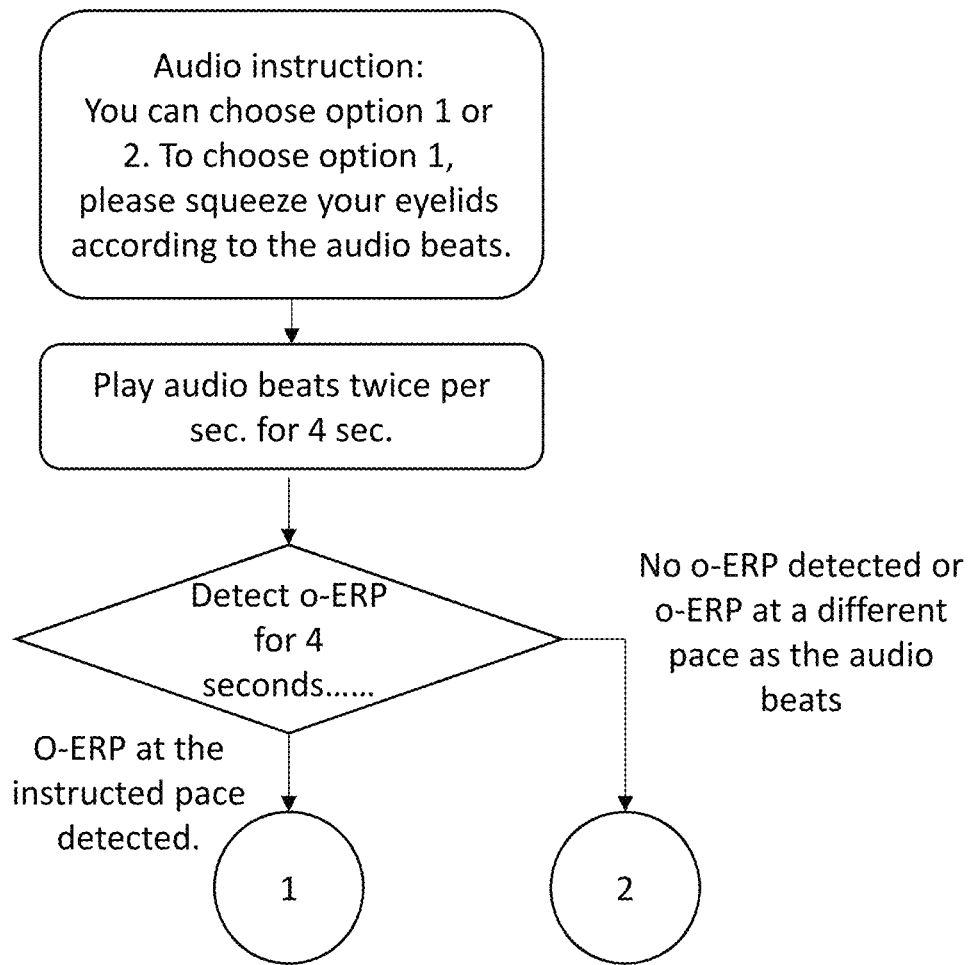

FIG. 9A-9E show an exemplary process of human-computer interaction and the recorded signals according to some embodiments of the present disclosure. FIG. 9A is a flowchart of the process according to some embodiments of the present disclosure. In some embodiments, the audio unit plays an audio instruction, teaching the user how to make a yes/no selection, followed by a series of rhythmic beats as an audio template. Then bioelectrical signal acquisition device 20 collects digital bioelectrical signals from the user and transmits the digital bioelectrical signals to the computational unit 31, where the signals are processed, and o-ERPs are identified and analyzed. Based on the presence and pattern of the o-ERP, the choice between yes and no can be made.

FIG. 9B shows an audio template at a pace of twice per second. This audio template was used in a test carried out according to FIG. 9A. The audio signals were a sequence of metronome ticks at a pace of twice per second.

FIG. 9C is a time-domain signal presentation, or wave chart, showing some exemplary results of a test that was carried out in the process shown in FIG. 9A, with a sequence of synchronized o-ERPs corresponding to the audio template shown in FIG. 9B. As shown in FIG. 9C, the user that squeezed his eyelids as instructed and provided the sequence of synchronized o-ERPs, which were detected by the bioelectrical signal acquisition device 20 and processed by the computational unit 31. The presence of the o-ERP was determined by setting proper thresholds for the amplitude. Based on the consistency of the o-ERP with the audio template, the choice between yes and no was made. FIG. 9D shows a frequency histogram with a peak at 2 Hz, consistent with the audio template shown in FIG. 9B.

FIG. 9E is a frequency-domain presentation, or a spectrogram, showing some exemplary results of the test that was carried out according to the process shown in FIG. 9A, with a sequence of synchronized o-ERPs corresponding to the audio template shown in FIG. 9B. The presence and pattern of the o-ERPs were detected by the bioelectrical signal acquisition device 20 and processed by the computational unit 31. The sequence of o-ERPs was detected with high-intensity spots, with a 2 Hz frequency.

In some embodiments, the signal sequence may include a signal template (e.g., an audio template) that include repeated signals. The user can follow an instruction (predetermined or real-time) and utilize the audio template as basis for input (e.g., by squeezing eyelid, making eye movement, etc.), forming patterns to make a choice or convey certain meanings. Such patterns may take the form of a binary sequence. For example, in certain embodiments, the patterns may be "*---*", "--**", "*--", "----*", etc. ("*" and "-" represent presence and absence of a blink, respectively).

Figure 10A:
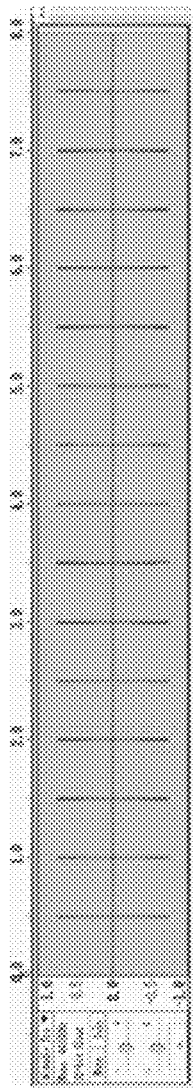
FIGS. 10A-10B show an exemplary audio signal template (FIG. 10A), a digital bioelectrical signal recording (FIG. 10B) in response to the audio signal template, and a corresponding result chart (FIG. 10C) of the digital bioelectrical signal recording, according to some embodiments of the present disclosure.
Figure 10B:
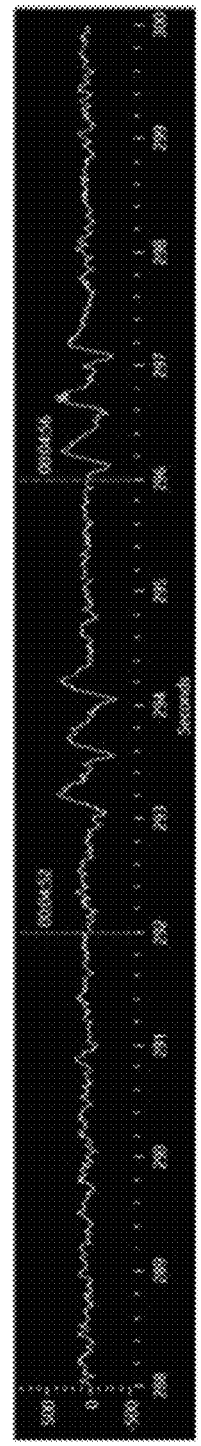
Figure 10C:
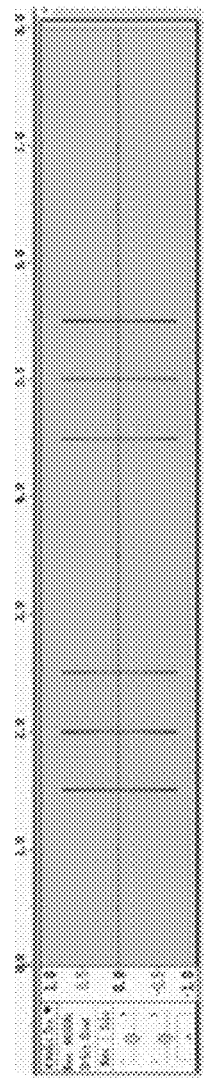

FIGS. 10A-10B show an exemplary audio signal template (FIG. 10A), a digital bioelectrical signal recording (FIG. 10B) in response to the audio signal template, and a corresponding result chart (FIG. 10C) of the digital bioelectrical signal recording, according to some embodiments of the present disclosure. When a user squeezed eyelids according to an instructed pattern, "*---*", at the rhythm given by the audio template (FIG. 10A), a binary sequence of synchronized o-ERPs was detected in the time-domain presentation, or the wave chart (FIG. 10B). The "*---*" pattern was recognized (FIG. 10C) in the time-domain presentation by setting proper thresholds for signal amplitude, or by using a template matching algorithm using a pattern-enveloped audio template (FIG. 10C). In some embodiments, the positive result may trigger further corresponding actions by the interactive system 50.

In some embodiments, the patterns can be sequences defined in Morse code, since it is a well-known binary sequence representing English alphabets. For example, the "*---*" pattern in FIG. 10C may be interpreted as "SOS" according to Morse code.

In certain scenario, when there is a high noise level in the data acquired by the bioelectrical signal acquisition device 20, it may be easier (i.e. with higher identification accuracy) to detect positive input (e.g., o-ERPs) with patterns (e.g. as the embodiment shown in FIGS. 10A-10C) than single input (e.g., as the embodiment shown in FIGS. 8A-8C).

Figure 11A:
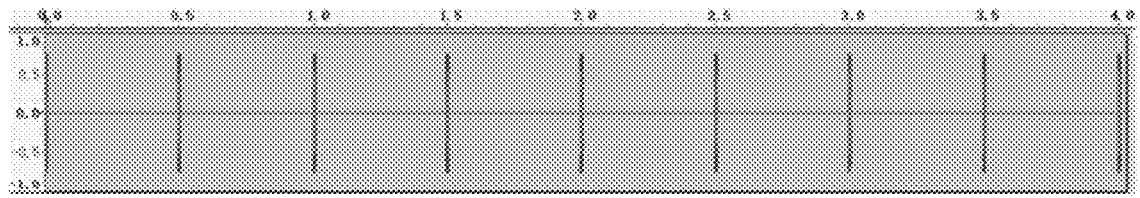
FIGS. 11A-11D show various exemplary audio signal templates according to some embodiments of the present disclosure.
Figure 11B:
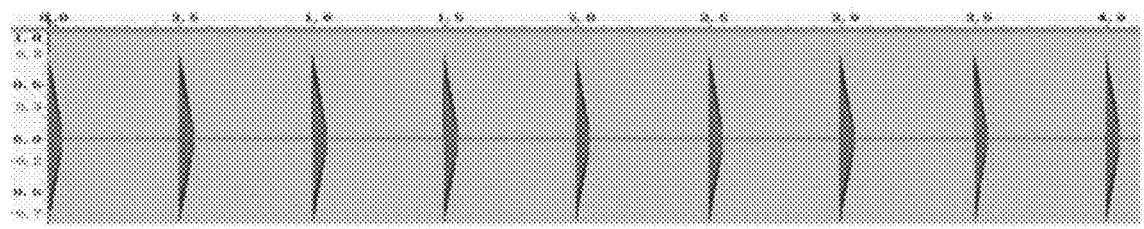
Figure 11C:
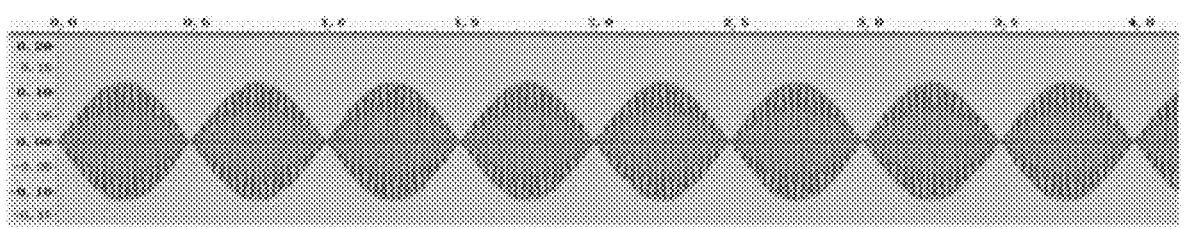
Figure 11D:
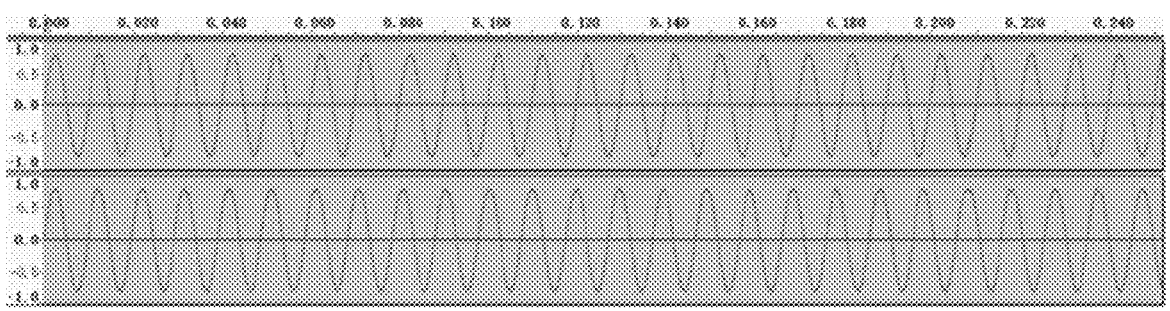

FIGS. 11A-11D show various exemplary audio signal templates according to some embodiments of the present disclosure. In some embodiments, the audio template may be a serious of beats, metronome, ding, chirp, ticking, amplitude-modulated tones or noises, frequency-modulated tones or noises, binaural beats, music pattern, or any form of rhythmic sound, binaural beats, music or other rhythmic sound tracks. For example, FIG. 11A shows clicks, FIG. 11B shows chirps, FIG. 11C shows amplitude modulated tones, and FIG. 11D shows binaural beats.

Figure 12A:
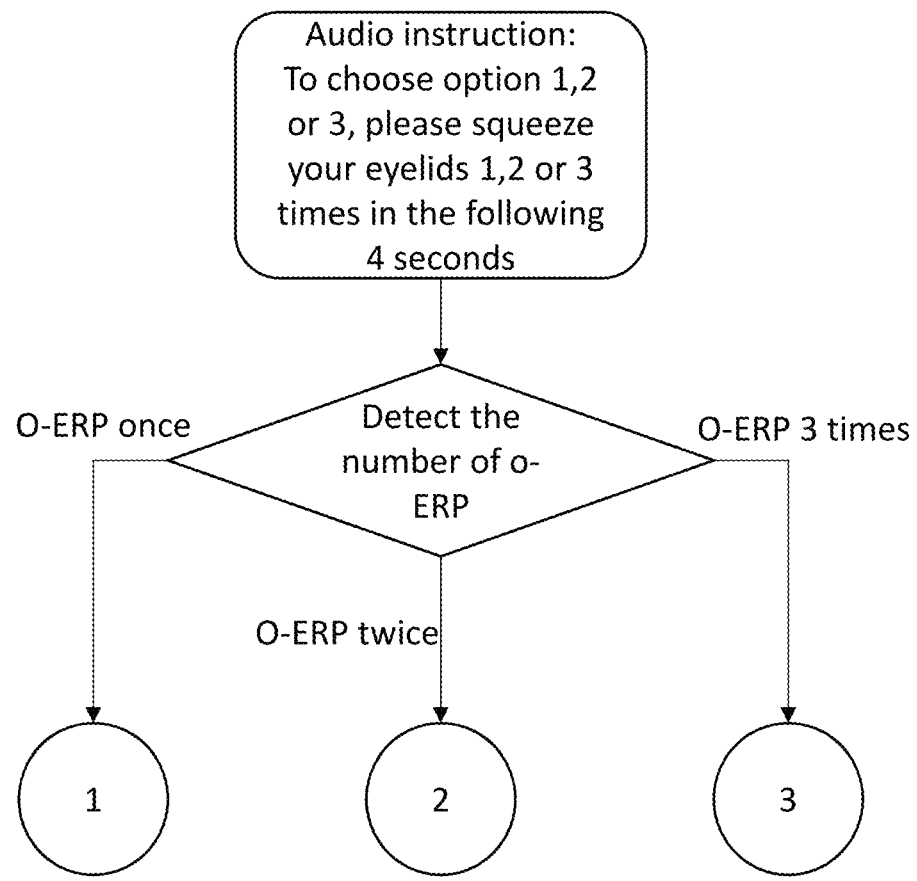
FIGS. 12A-12C shows an exemplary process of human-computer interaction and the recorded digital bioelectrical signals collected from a user's head by the bioelectrical signal acquisition device according to some embodiments of the present disclosure.
Figure 12B:
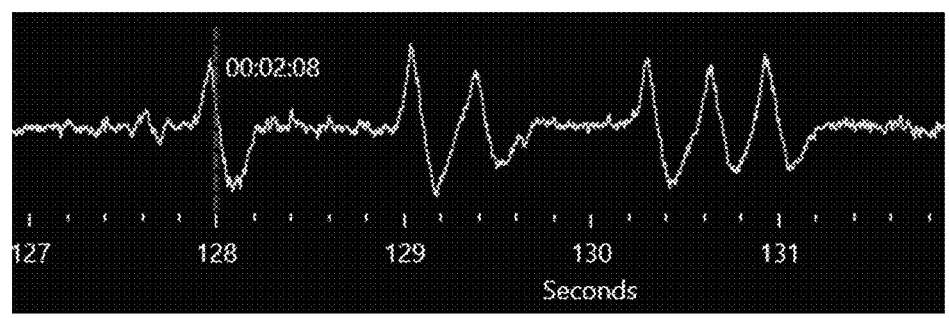
Figure 12C:
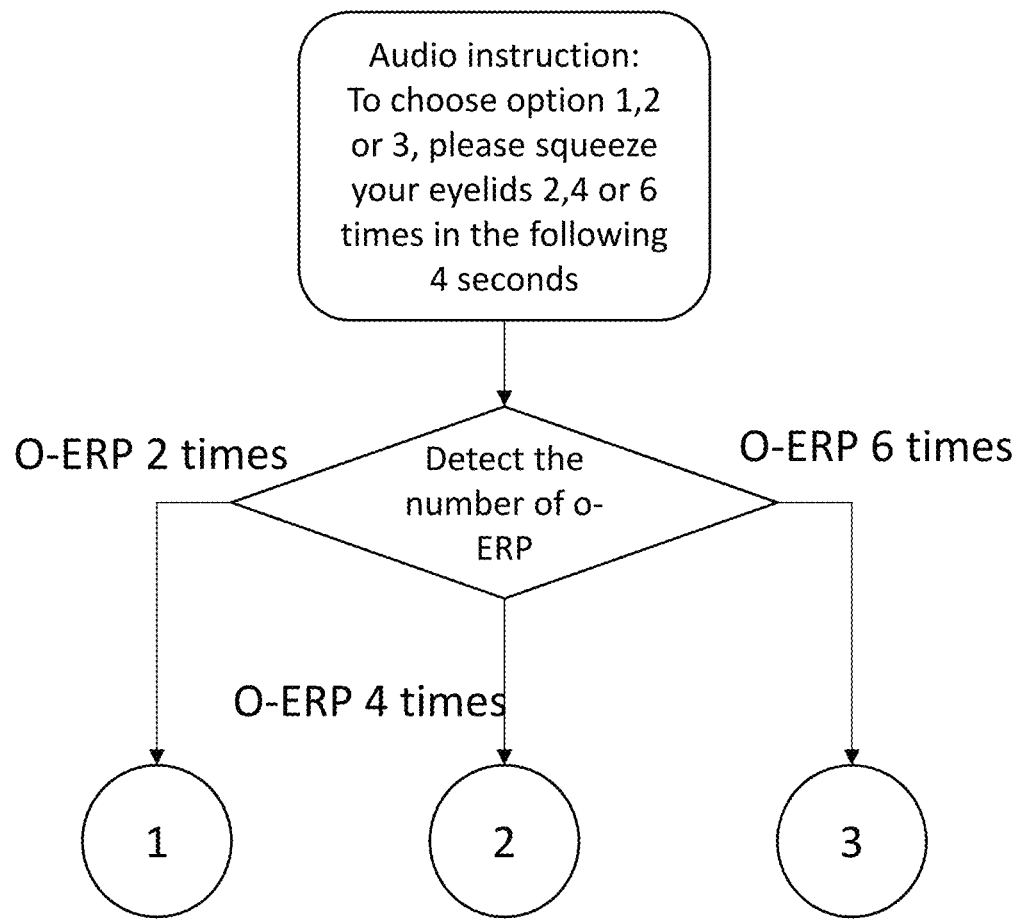

FIGS. 12A-12C shows an exemplary process of human-computer interaction and the recorded digital bioelectrical signals collected from a user's head by the bioelectrical signal acquisition device according to some embodiments of the present disclosure.

FIG. 12A is a flowchart of the process in which the user is presented with multiple choices. In some embodiments, the audio unit plays an audio instruction, teaching the user how to make a multiple-choice selection, by squeezing eyelids for the number of times that the user intends to choose. Then bioelectrical signal acquisition device 20 collects digital bioelectrical signals from the user and transmits the digital bioelectrical signals to the computational unit 31, where the signals are processed, and o-ERPs are identified and analyzed. Based on the number of the o-ERPs, the choice is made.

FIG. 12B is a time-domain signal presentation, or wave chart, showing some exemplary results of a test that was carried out in the process shown in FIG. 12A. As shown in FIG. 12B, the user that squeezed his eyelids as instructed and the o-ERPs were detected by the bioelectrical signal acquisition device 20 and processed by the computational unit 31. The presence and the number of the o-ERPs were determined by setting proper thresholds for the amplitude. When there are 1, 2 and 3 o-ERPs (from left to right), there are 1, 2 and 3 high amplitude main peaks. Therefore, the identification of the o-ERP can be determined by setting proper thresholds for the amplitude and counting the number of main peaks.

In some embodiments, the number of o-ERPs can be identified by other methods, such as detecting long gaps between zero-crosses in time domain data, or template matching with a predefined o-EPR template.

FIG. 12C provides an alternative process similar to the process shown in FIG. 12A. In some embodiments, the number of choices may be more than 3. With the same logic principle as shown in FIG. 12A, the method can apply to any number of choices, simply by adding the more choices in the instruction, as well as the o-ERP identification process, as shown in FIG. 12C, in which the user is instructed to squeeze eyelids for 2, 4, or 6 times to choose options 1, 2, and 3, respectively. In certain embodiments, it is more accurate to differentiate between 2, 4, and 6 o-ERPs than to differentiate between 1, 2, and 3 o-ERP, especially when noise is high.

Figure 13A:
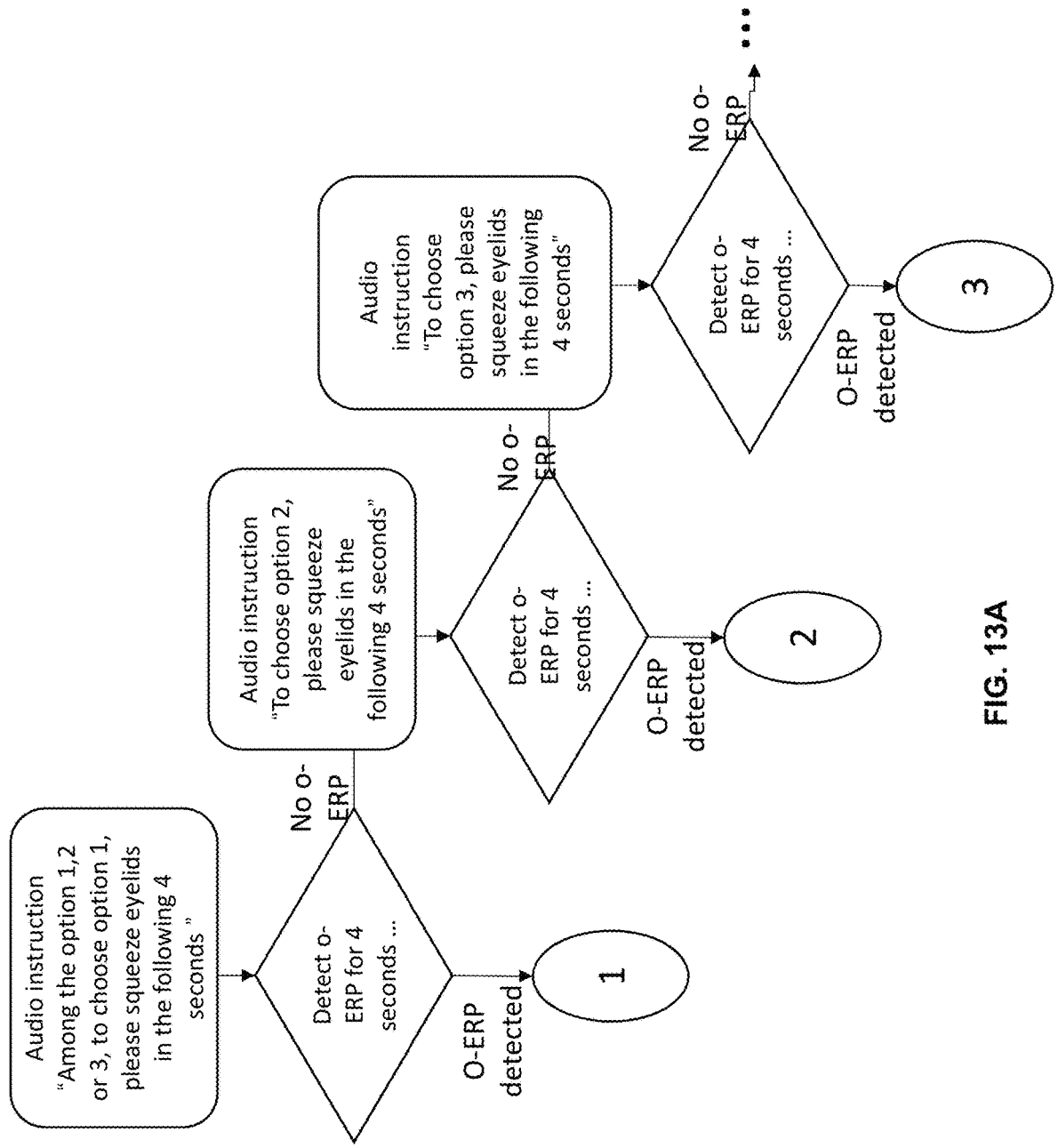
FIGS. 13A-13B show an exemplary process of human-computer interaction and the recorded digital bioelectrical signals collected from a user's head by the bioelectrical signal acquisition device according to some embodiments of the present disclosure.
Figure 13B:
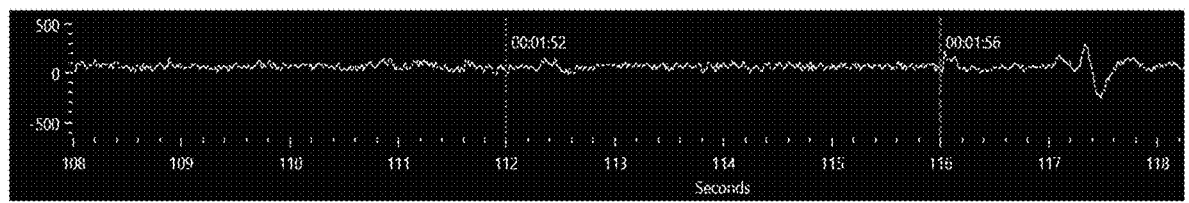

FIGS. 13A-13B show an exemplary process of human-computer interaction and the recorded digital bioelectrical signals collected from a user's head by the bioelectrical signal acquisition device according to some embodiments of the present disclosure; FIG. 13A is a flowchart of the process according to some embodiments of the present disclosure; FIG. 13B is time-domain signal presentation, or wave chart.

FIG. 13A is a flowchart of the process in which the user is presented with multiple choices. In some embodiments, the audio unit plays an audio instruction, teaching the user how to make a multiple-choice selection, by squeezing eyelids after the desired option is presented and before the next option is presented. Then bioelectrical signal acquisition device 20 collects digital bioelectrical signals from the user and transmits the digital bioelectrical signals to the computational unit 31, where the signals are processed, and o-ERPs are identified and analyzed. Based on the presence of o-ERP detected within the defined time frame, the choice is made.

FIG. 13B is a time-domain signal presentation, or wave chart, showing some exemplary results of a test that was carried out in the process shown in FIG. 13A, As shown in FIG. 13B, the user that squeezed his eyelids as instructed and the o-ERP was detected by the bioelectrical signal acquisition device 20 and processed by the computational unit 31. The presence of the o-ERPs was determined by setting proper thresholds for the amplitude. An o-ERP was detected in the third time frame, but not in the first two time frames.

Figure 14:
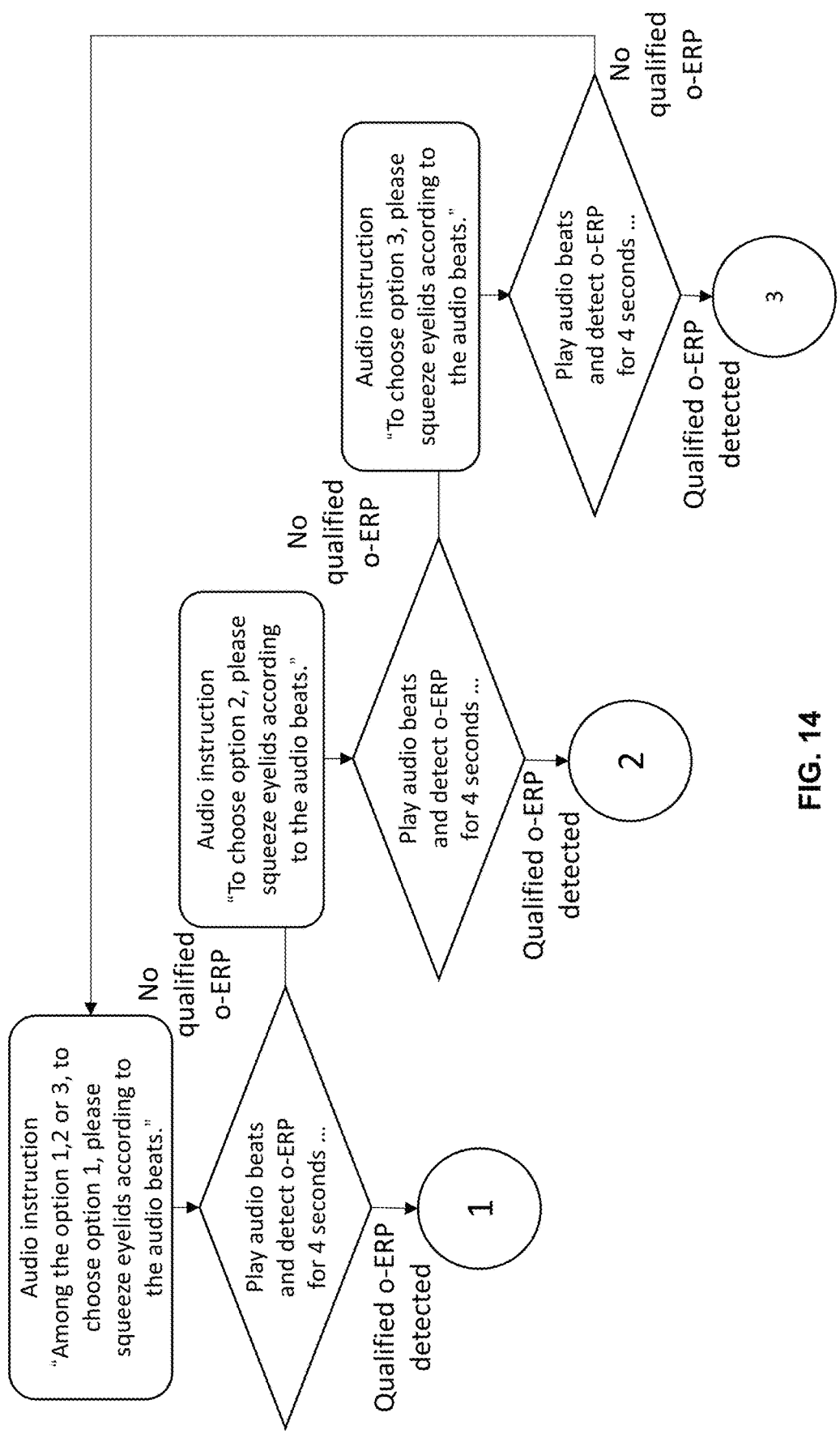
FIG. 14 is a flowchart showing an exemplary process of human-computer interaction according to some embodiments of the present disclosure.

FIG. 14 is a flowchart showing an exemplary process of human-computer interaction according to some embodiments of the present disclosure. The embodiment shown in FIG. 14 demonstrates that the menu may be on any question and the logic cycle can extend indefinitely.

Comparing to the embodiments shown in the FIGS. 12A-12C, the cascade menu selection approach shown in FIGS. 13-14 releases the user from the burden of memorizing the number of choice and accurately squeeze the intended number of times. In certain scenarios, it is a preferable approach when the list of options is long.

Figure 15:
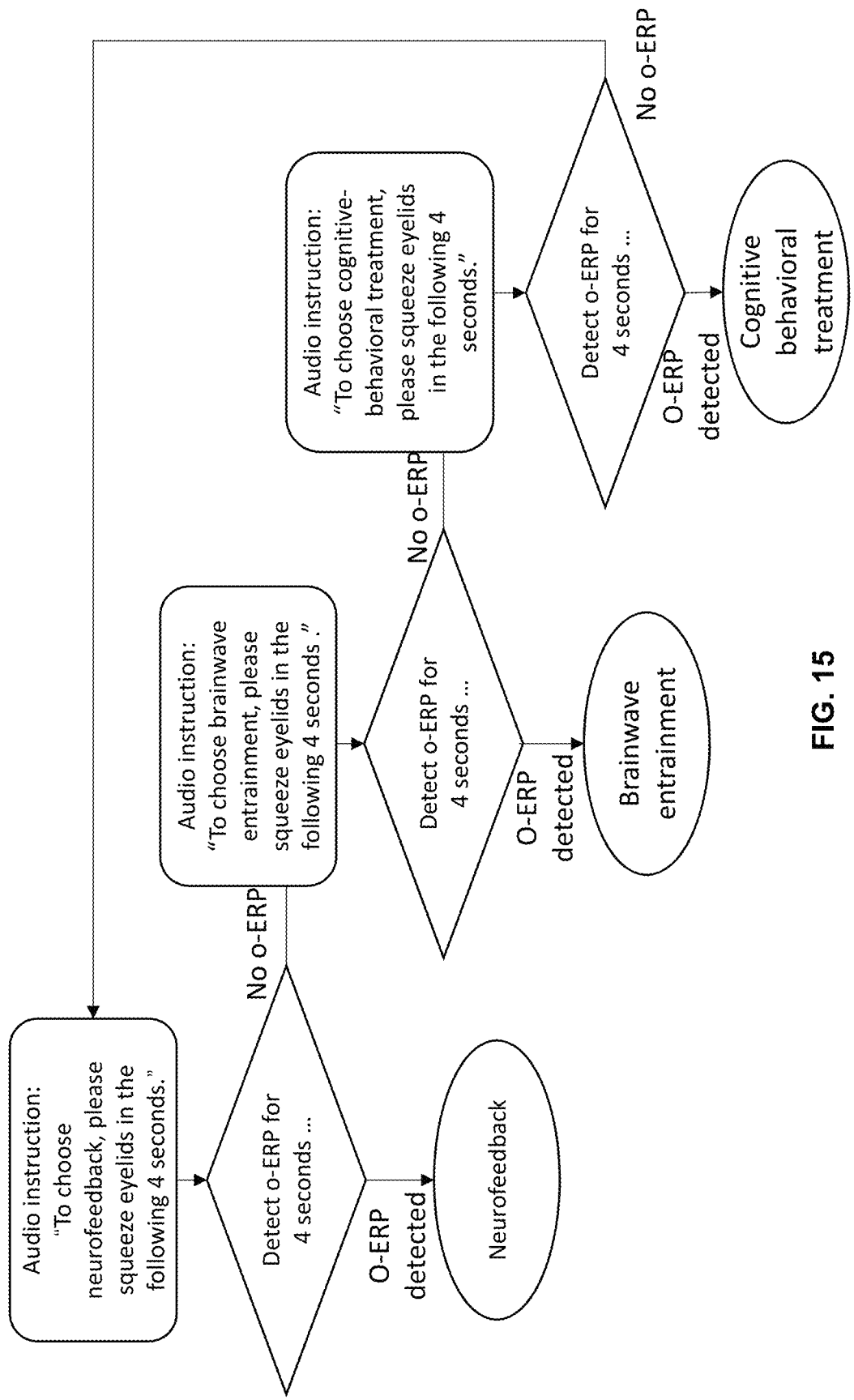
FIG. 15 is a flowchart showing an exemplary process of human-computer interaction according to some embodiments of the present disclosure.

FIG. 15 is a flowchart showing an exemplary process of human-computer interaction according to some embodiments of the present disclosure. The embodiment shown in FIG. 15 demonstrates an example of more than one method being combined, to realized high selection accuracy on multiple-choice questions.

Figure 16:
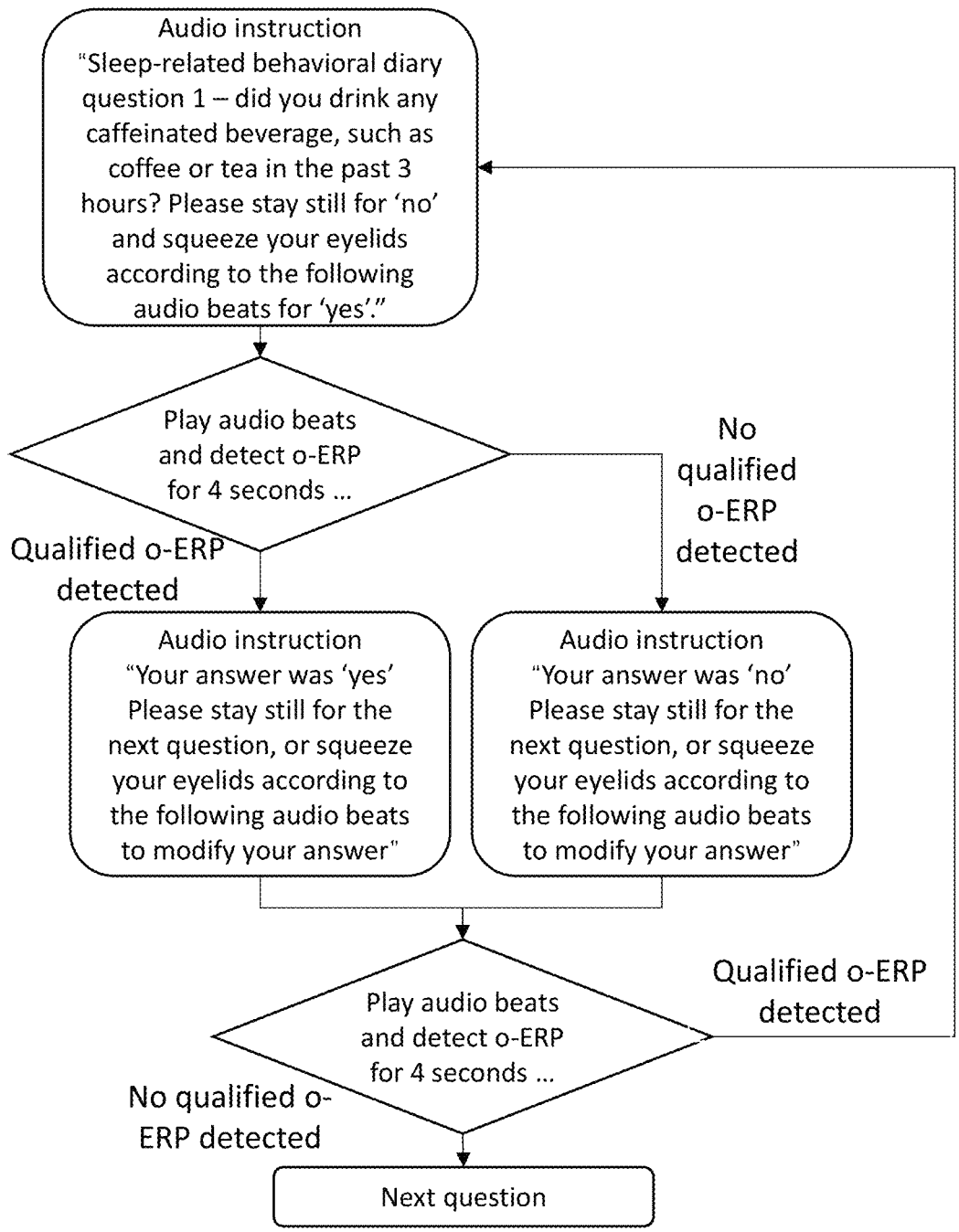
FIG. 16 is a flowchart showing an exemplary process of human-computer interaction according to some embodiments of the present disclosure.

FIG. 16 is a flowchart showing an exemplary process of human-computer interaction according to some embodiments of the present disclosure. The embodiment shown in FIG. 16 demonstrates an example of fail-safe logic to allow user to confirm or reject the choice just made.

Figure 17:
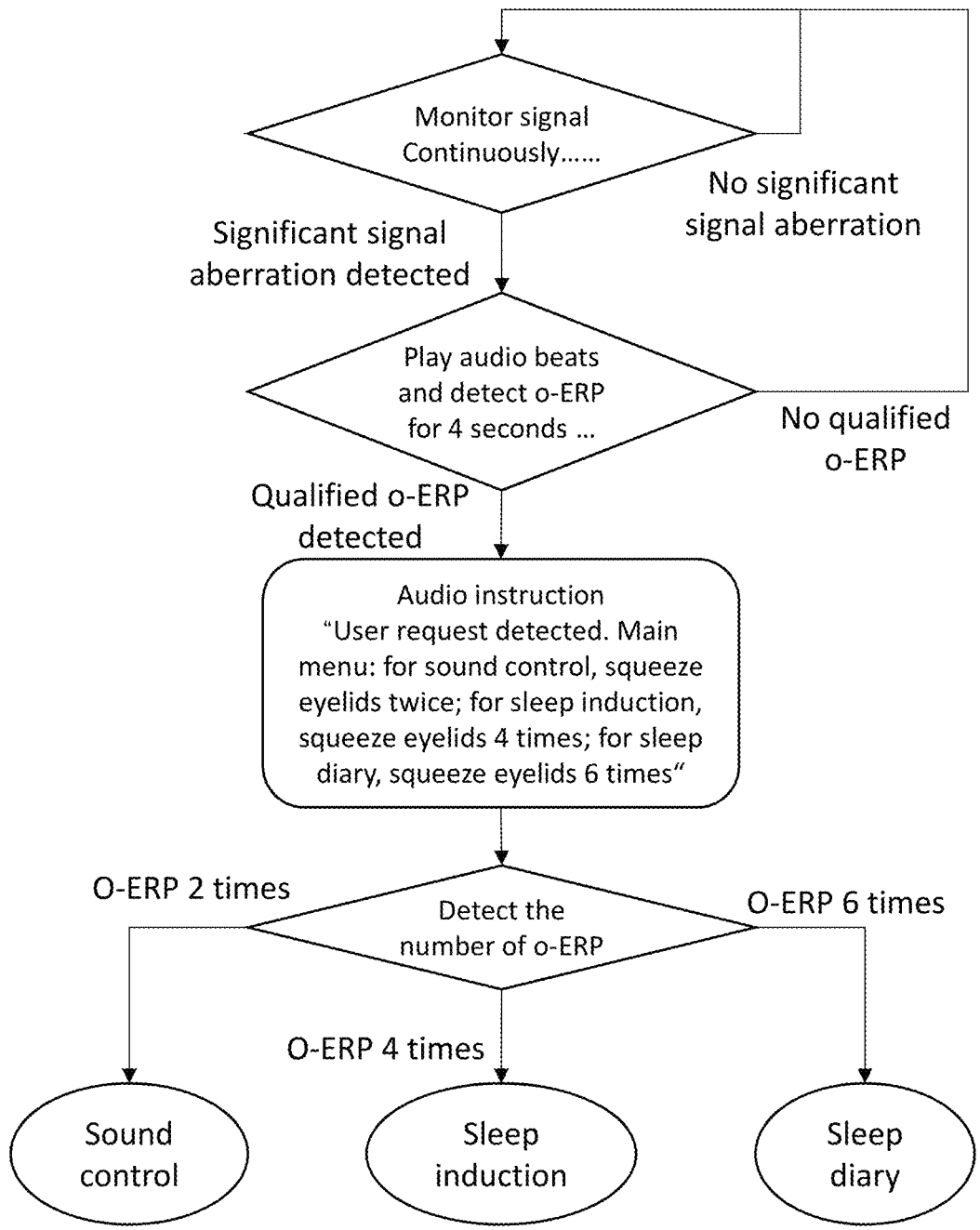
FIG. 17 is a flowchart showing an exemplary process of human-computer interaction according to some embodiments of the present disclosure.

FIG. 17 is a flowchart showing an exemplary process of human-computer interaction according to some embodiments of the present disclosure. The embodiment shown in FIG. 17 demonstrates an example of a mechanism to initiate the human-computer interaction from an idle state, by bring the menu up to the user when there is no active interaction.

Typically, when a user is asleep or ready to sleep, the signals collected by the bioelectrical signal acquisition device 20 are mainly low amplitude EEG signals. When a significant aberrant signal is detected, it is usually due to EOG or EMG artifacts commonly associated with user's eye movements, facial movements or head movements, either voluntarily or involuntarily. When such events take place, the device may present a weak rhythmic audio template. If the user intends to activate the menu, he or she can certain actions (e.g., squeeze eyelids) according to the audio template, and further instructions and menu may be presented through the audio playing unit. If the user doesn't want to activate the menu, or the artifact was simply from sleep posture adjustment, REM or some other incident, user will not carry out the specific eye movement set by the audio template, and the interactive system 50 will return to regular recording state and continue to monitor the signals.

Having thus described the basic concepts, it may be rather apparent to those skilled in the art after reading this detailed disclosure that the foregoing detailed disclosure may be intended to be presented by way of example only and may be not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment may be included in at least one embodiment of the present disclosure. Therefore, it may be emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that may be not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object to be recognized oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local part network (LAN) or a wide part network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, may be not intended to limit the claimed processes and methods to any order except as may be specified in the claims. Although the above disclosure discusses through various examples what may be currently considered to be a variety of useful embodiments of the disclosure, it may be to be understood that such detail may be solely for that purposes, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purposes of streamlining the disclosure aiding in the understanding of one or more of the various inventive embodiments. This method of disclosure, however, may be not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein may be hereby incorporated herein by this reference in its entirety for all purposes, excepting any prosecution file history associated with same, any of same that may be inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

Statements of Invention
Device

Section 1.1. A bioelectrical signal acquisition device, comprising:
a headband configured to be wearable around a user's head,
 a sensing electrode attached to the headband;
 a reference electrode attached to the headband;
 wherein the sensing electrode and the one or more reference electrodes are configured to provide sensing signals from the user's head, and the reference electrode is configured to cover at least part of a bottom side of a segment of the headband, and
 a processing unit configured to generate digital bioelectrical signals based on the sensing signals.

Section 1.2. The bioelectrical signal acquisition device of Section 1.1, further comprising a grounding electrode attached to the headband and configured to provide electronic grounding, wherein the grounding electrode is positioned on the headband to contact the user's skin, when the user wears the bioelectrical signal acquisition device on the user's head.

Section 1.3. The bioelectrical signal acquisition device of Section 1.1, wherein the sensing electrode is positioned on the headband to contact the skin on the forehead or around the eyes of the user, and the reference electrode is positioned on the headband to contact the skin on, over, above, behind, or around an ear of the user, when the user wears the bioelectrical signal acquisition device on the user's head.

Section 1.4. The bioelectrical signal acquisition device of Section 1.1, wherein the reference electrode is configured to cover a lower portion of the bottom side of the segment of the headband.

Section 1.5. The bioelectrical signal acquisition device of Section 1.1, wherein the reference electrode is configured to cover a lower portion of the bottom side and a lower edge of the segment of the headband.

Section 1.6. The bioelectrical signal acquisition device of Section 1.1, wherein the reference electrode is configured to cover the entire bottom side and a lower edge of the segment of the headband.

Section 1.7. The bioelectrical signal acquisition device of any of Sections 1.1-1.6, wherein the processing unit comprises an electrical signal amplification circuit configured to amplify the sensing signals; and an analog-to-digital converting circuit configured to convert analog signals to digital signals.

Section 1.8. The bioelectrical signal acquisition device of Sections 1.1-1.7, future comprising signal wires connecting the sensing electrode and the reference electrodes to an input port of the signal amplification circuit.

Section 1.9. The bioelectrical signal acquisition device of any of Sections 1.2-1.8, wherein at least a portion of the wires are shielded wires comprising a shielding layer, and the shielding layer is connected to the grounding electrode.

Section 1.10. The bioelectrical signal acquisition device of any of Sections 1.1-1.9, further comprising a transmission element configured to transmit the digital bioelectrical signals to a computational unit via wire or with wireless transmission.

Section 1.11. The bioelectrical signal acquisition device of Section 1.10, wherein the wireless transmission is through BLUETOOTH or WIFI.

Section 1.12. The bioelectrical signal acquisition device of any of Sections 1.1-1.11, which is a single-channel bioelectrical signal recorder.

Section 1.13. The bioelectrical signal acquisition device of any of Sections 1.1-1.11, which is a multiple-channel bioelectrical signal recorder.

Section 1.14. The bioelectrical signal acquisition device of any of Sections 1.1-1.13, comprising two reference electrodes attached to the headband, wherein each of the reference electrodes is positioned on the headband to contact the skin above an ear of the user, when the user wears the bioelectrical signal acquisition device on the user's head.

Section 1.15. The bioelectrical signal acquisition device of any of Sections 1.2-1.14, wherein the sensing electrode and the grounding electrode are positioned on the headband to contact the skin on the forehead or around the eyes, symmetrical of a sagittal plane of the user's body, when the user wears the bioelectrical signal acquisition device on the user's head.

Section 1.16. The bioelectrical signal acquisition device of any of Sections 1.2-1.15, wherein the sensing electrode, the reference electrode, and the grounding electrode are integrated in the headband.

Section 1.17. The bioelectrical signal acquisition device of Section 1.16, wherein the sensing electrode, the reference electrode, and the grounding electrode are integrated in the headband to not disturb the user when the user sleeps or prepares to fall asleep.

Section 1.18. The bioelectrical signal acquisition device of any of Sections 1.1-1.17, wherein the headband is made from soft and elastic material and configured to not disturb the user when the user sleeps or prepares to fall asleep.

Section 1.19. The bioelectrical signal acquisition device of any of Sections 1.8-1.18, wherein the signal wires are integrated in the headband and configured to not disturb the user when the user sleeps or prepares to fall asleep.

Section 1.20. The bioelectrical signal acquisition device of any of Sections 1.1-1.18, wherein the reference electrode comprises conductive fibric.

Section 1.21. The bioelectrical signal acquisition device of any of Sections 1.1-1.18, wherein the reference electrode is configured to encircle the segment of the headband.

Section 1.22. The bioelectrical signal acquisition device of any of Sections 1.1-1.21, wherein the digital bioelectrical signals comprise electroencephalogram (EEG), electromyogram (EMG), and/or Electrooculography (EOG) signals of the user when the user sleeps or prepares to fall asleep.

Section 1.23. The bioelectrical signal acquisition device of any of Sections 1.1-1.21, wherein the digital bioelectrical signals comprise EEG signals of the user when the user sleeps or prepares to fall asleep.

Section 1.24. The bioelectrical signal acquisition device of any of Sections 1.1-1.21, wherein the digital bioelectrical signals comprise EEG and EOG signals of the user when the user sleeps or prepares to fall asleep.

System

Section 2.1. An interactive system, comprising:

the bioelectrical signal acquisition device of any of Sections 1.1-1.24, and a computational unit configured to receive the digital bioelectrical signals from the bioelectrical signal acquisition device, process the digital bioelectrical signals and execute one or more logic sets based on the digital bioelectrical signals.

Section 2.2. The interactive system of Section 2.1, which is configured to monitor sleep patterns of the user when the user sleeps or prepares to fall asleep.

Section 2.3. The interactive system of Section 2.1, which is configured to monitor existence and pattern of ocular event-related potentials (o-ERPs).

Section 2.4. The interactive system of Section 2.3, which is configured to monitor eye blink, eye movement, or eyelid squeezing by processing the digital bioelectrical signals.

Section 2.5. The interactive system of any of Sections 2.1-2.2, wherein the computational unit is a personal computer, a tablet computer, a smart phone, a generic microprocessor, or a specialized microprocessor.

Section 2.6. The interactive system of Section 2.5, wherein the computational unit is structurally independent from, an integrated component of, an accessory of, or an extension of the bioelectrical signal acquisition device.

Section 2.7. The interactive system of any of Sections 2.1-2.6, wherein the computational unit further comprises a low-pass filter, a high-pass filter, or a band-pass filter, or a combination thereof, configured to conduct a digital filtering process on the digital bioelectrical signals.

Section 2.8. The interactive system of any of Sections 2.1-2.7, further comprising an audio unit, which is configured to provide audio signals to the user.

Section 2.9. The interactive system of Section 2.8, wherein the audio unit includes an audio earplug, a pair of audio-earplugs, a headset, or a speaker.

Section 2.10. The interactive system of any of Sections 2.7-2.8, wherein the audio unit is operationally connected to the computational unit and provides audio signals under control of the computational unit.

Section 2.11. The interactive system of any of Sections 2.7-2.10, wherein the audio unit is structurally independent from, an integrated component of, an accessory of, or an extension of the computational unit.

Section 2.12. The interactive system of any of Sections 2.4-2.7, wherein the audio unit connects to the computational unit via wire or wireless connection.

Method 1

Section 3.1. A method of monitoring sleep patterns of a user, comprising:

providing an interactive system of any of Sections 2.1-2.12;

collecting the digital bioelectrical signals of the user with the bioelectrical signal acquisition device when the user sleeps or prepares to fall asleep; and processing the digital bioelectrical signals with the computational unit to monitor the sleep patterns of the user.

Section 3.2. The method of Section 3.1, wherein the digital bioelectrical signals include EEG, EOG, or EMG signals, or any combination thereof.

Section 3.3. The method of Section 3.1, wherein the processing the digital bioelectrical signals includes wave analysis of time-domain signals and spectrum analysis of frequency-domain signals.

Section 3.4. The method of Section 3.1, wherein the sleep patterns include sleep stage, sleep depth and derived results, including total sleep time, onset latency, wake after sleep onset, and sleep efficiency.

Method 2

Section 4.1. A method of human-computer interaction using an interactive system, comprising:

providing a signal sequence to the user;

recording digital bioelectrical signals from the user's head using a bioelectrical signal acquisition device;

processing the digital bioelectrical signals and identifying the existence and the pattern of ocular event-related potentials (o-ERPs); and taking one or more actions based on the existence and the patterns of the o-ERPs.

Section 4.2. The method of Section 4.1, wherein the interactive system is the interactive system of Sections 2.1-2.12.

Section 4.3. The method of Section 4.2, wherein the digital bioelectrical signals from the user's head are collected by the bioelectrical signal acquisition device of Sections 1.1-1.24.

Section 4.4. The method of Section 4.2, wherein the digital bioelectrical signals are processed by the computational unit.

Section 4.5. The method of any of Sections 4.1-4.4, wherein providing the signal sequence to the user comprises touching the user, sending vibration to the user, playing sound to the user, or applying light to the user, or any combinations thereof.

Section 4.6. The method of any of Sections 4.5, wherein signal sequence includes: a description, a question, or an instruction, or any combination thereof, all relating to upcoming interactions between the user and the interactive system.

Section 4.7. The method of Section 4.6, wherein providing the signal sequence to the user comprises playing a plurality of sounds to the user with the audio unit in any of Sections 2.4-2.9.

Section 4.8. The method of any of Sections 4.6-4.7, wherein the description includes an explanation of the upcoming interactions, and the explanation is about context, or past, current and expected logic states of the upcoming interactions.

Section 4.9. The method of any of Sections 4.6-4.8, wherein the question includes a presentation of one or more questions and list of choices for the upcoming interactions.

Section 4.10. The method of any of Sections 4.6-4.9, wherein the instruction includes information on how to provide a response, preferably making a selection among the choices presented in Section 4.6.

Section 4.11. The method of Section 4.10, wherein providing a response includes eye blink, eye movement, or eyelid squeezing, or any combination thereof, by the user.

Section 4.12. The method of any of Sections 4.7-4.11, wherein the plurality of sounds include one or more rhythmic audio templates.

Section 4.13. The method of Section 4.12, wherein the rhythmic audio templates include sounds of beats, metronome, ding, chirp, ticking, amplitude-modulated tones or noises, frequency-modulated tones or noises, binaural beats, music pattern, or any form of rhythmic sound.

Section 4.14. The method of Section 4.13, wherein the rhythmic audio templates have a rhythmic frequency between 0.5 Hz and 4 Hz, preferably between 1 Hz and 2 Hz.

Section 4.15. The method of any of Sections 4.1-4.14, wherein the o-ERPs result from eye blinking, eye movement, or eyelid squeezing, or any combination thereof, by the user.

Section 4.16. The method of any of Sections 4.1-4.15, wherein the digital bioelectrical signals have a sample rate ranging from 100 samples per second to 10000 samples per second, preferably from 250 to 1000 samples per second.

Section 4.17. The method of any of Sections 4.1-4.16, wherein processing the digital bioelectrical signals includes a digital filtering process, using a low-pass filter, a high-pass filter, or a band-pass filter, or a combination thereof.

Section 4.18. The method of Section 4.17, wherein processing the digital bioelectrical signal includes applying a fast Fourier transform (FFT) to data derived from the digital bioelectrical signals to generate a frequency-domain presentation.

Section 4.19. The method of Section 4.18, wherein processing the digital bioelectrical signal further includes applying a window function to the data derived from the digital bioelectrical signals before the FFT.

Section 4.20. The method of Section 4.18, wherein processing the digital bioelectrical signal further includes applying a zero-padding step before applying the FFT transformation to raise a number of samples by an $N^{th}$ order of 2, where N is a positive integer.

Section 4.21. The method of Section 4.18, wherein processing the digital bioelectrical signal further includes applying a step of down sampling before the FFT, reducing the sample rate between 100 and 1000, preferably between 120 and 300.

Section 4.22. The method of any of Sections 4.1-4.21, wherein identifying the o-ERPs is based on a time-domain presentation, also known as a wave chart, wherein an x-axis represents time, and a y-axis represents the amplitude of an electrical voltage.

Section 4.23. The method of any of Sections 4.1-4.21, wherein identifying the o-ERPs is based on a frequency-domain presentation, also known as a spectrogram, wherein an x-axis represents time, and a y-axis represents frequencies.

Section 4.24. The method of any of Sections 4.1-4.21, wherein identifying the o-ERPs is based on a pattern recognition of the o-ERPs based on one or more thresholds in the time-domain presentation, or one or more thresholds in frequency-domain presentation.

Section 4.25. The method of Section 4.24, wherein the pattern recognition of the o-ERPs includes a template matching algorithm, utilizing a template selected from sine waves, triangle wave, rectangle waves, and other periodic waves with the same frequency as the audio's rhythm, enveloped by the binary sequence from the pattern.

Section 4.26. The method of any of Sections 4.1-4.25, wherein the one or more actions include triggering one or more steps of conditional choices.

Section 4.27. The method of any of Sections 4.1-4.26, wherein one step of the conditional choices includes a binary-choice conditional branch, which is triggered by a presence of a detected o-ERP during a pre-determined time period.

Section 4.28. The method of any of Sections 4.1-4.26, wherein one step of the conditional choices includes a multiple-choice conditional branch, which is triggered by two or more detected o-ERPs during a pre-determined time period.

Section 4.29. The method of any of Sections 4.1-4.28, wherein the one or more actions are taken by the computational unit, the audio unit, or the bioelectrical signal acquisition device.

Section 4.30. The method of Section 4.29, wherein the action includes: playing additional sounds with increased or decreased volume, playing a pre-recorded audio file, repeating a previous question, triggering a function menu, starting an insomnia treatment session, starting recording sound, sending a message, or sharing current sleep status in social media, or any combination thereof.

Method 5

Section 5.1. A method of detecting ocular event-related potentials (o-ERPs), comprising:
recording digital bioelectrical signals from the user's head using a bioelectrical signal acquisition device; and
processing the digital bioelectrical signals with a computational unit and identifying the existence and the pattern of ocular event-related potentials (o-ERPs).

Section 5.2. The method of Section 5.1, wherein the bioelectrical signal acquisition device and the computational unit are from the interactive system of any of Sections 2.1-2.12.

Section 5.3. The method of any of Sections 5.1-5.2, wherein the o-ERPs result from eye blink, eye movement, or eyelid squeezing, or any combination thereof, by the user.

Section 5.4. The method of any of Sections 5.1-5.3, wherein the digital bioelectrical signals have a sample rate ranging from 100 samples per second to 10000 samples per second, preferably from 250 to 1000 samples per second.

Section 5.5. The method of any of Sections 5.1-5.4, wherein processing the digital bioelectrical signals includes a digital filtering process using a low-pass filter, a high-pass filter, or a band-pass filter, or a combination thereof.

Section 5.6. The method of Section 5.5, wherein a filter type is used in the digital filtering process, and the filter type is Butterworth, Chebyshev 1, Chebyshev 2, or Elliptic.

Section 5.7. The method of any of Sections 5.5-5.6, wherein: the low-pass filter has a cut-off frequency that is between 4 Hz and 48 Hz, preferable between 35 and 45 Hz; and the low-pass filter has a number of order that is between 1 and 14, preferable between 8 and 12.

Section 5.8. The method of any of Sections 5.5-5.7, wherein the low-pass filter is 10th order Butterworth with a cut-off at 40 Hz.

Section 5.9. The method of any of Sections 5.5-5.7, wherein the low-pass filter has a lower cut-off frequency between 0.25 Hz and 2 Hz, preferable between 0.5 Hz and 1 Hz.

Section 5.10. The method of any of Sections 5.5-5.6, wherein: the band-pass filter has an upper frequency limit between 4 Hz and 48 Hz, preferable between 35 Hz and 45 Hz; and the band-pass filter has a lower frequency limit between 0.25 Hz and 2 Hz, preferable between 0.5 Hz and 1 Hz.

Section 5.11. The method of any of Sections 5.1-5.10, wherein processing the digital bioelectrical signal includes applying a fast Fourier transform (FFT) to data derived from the digital bioelectrical signals to generate a frequency-domain presentation.

Section 5.12. The method of Section 5.11, wherein processing the digital bioelectrical signal further includes applying a window function to the data derived from the digital bioelectrical signals before the FFT.

Section 5.13. The method of Section 5.12, wherein the window function includes rectangular window, triangular window, Parzen window, Welch window, sine window, cosine-sum window, Hann window, Hamming window, Blackman window, or Nattall window, or other common window functions in the field of digital signal processing; preferably a Hann window.

Section 5.15. The method of any of Sections 5.12-5.13, wherein the window function has a window size ranging between 100 to 100000 samples, preferably collected in N seconds, where N is a positive integer.

Section 5.15. The method of any of Sections 5.11-5.14, wherein processing the digital bioelectrical signal further includes applying a zero-padding step before applying the FFT transformation to raise a number of samples by an $N^{th}$ order of 2, where N is a positive integer.

Section 5.16. The method of any of Sections 5.11-5.15, wherein processing the digital bioelectrical signal further includes applying a step of down sampling before the FFT, reducing the sample rate between 100 and 1000, preferably between 120 and 300.

Section 5.17. The method of any of Sections 5.1-5.16, wherein identifying the o-ERPs is based on a time-domain presentation, also known as a wave chart, wherein an x-axis represents time, and a y-axis represents the amplitude of an electrical voltage on.

Section 5.18. The method of any of Sections 5.1-5.16, wherein identifying the o-ERPs comprises identifying patterns in a time-domain presentation, with a threshold range from 5 to 300 uV, preferably between 20 to 100 uV.

Section 5.19. The method of any of Sections 5.1-5.16, wherein identifying the o-ERPs comprises detecting long gaps between zero-crosses in the time-domain presentation, with a threshold range from 0.01 second to 0.2 second, preferably between 0.05 second to 0.15 second.

Section 5.20. The method of any of Sections 5.1-5.16, wherein identifying the o-ERPs comprises template matching with a predefined o-EPR template in the time-domain presentation, with a matching score threshold range from 20 to 90, preferably between 60 to 80.

Section 5.21. The method of any of Sections 5.1-5.16, wherein identifying the o-ERPs is based on a frequency-domain presentation, also known as a spectrogram, wherein an x-axis represents time, and a y-axis represents frequencies.

Section 5.22. The method of any of Sections 5.1-5.16, wherein identifying the o-ERPs is based on a pattern recognition of the o-ERPs based on identifying patterns outside a first threshold range in the time-domain presentation, or identifying patterns outside a second threshold range in the frequency-domain presentation.

Section 5.23. The method of Section 5.22, wherein the pattern recognition of the o-ERPs includes a template matching algorithm, utilizing a template selected from sine waves, triangle wave, rectangle waves, and other periodic waves with the same frequency as the audio's rhythm, enveloped by the binary sequence from the pattern.

What is claimed is:

1. A method of human-computer interaction using an interactive system that includes a computational unit and a bioelectrical signal acquisition device, comprising:
    providing a signal sequence to the user with the computational unit;
    recording digital bioelectrical signals from the user's head using the bioelectrical signal acquisition device;
    processing the digital bioelectrical signals with the computational unit to identify the existence and the pattern of ocular event-related potentials (o-ERPs) by setting a threshold range and analyzing the digital bioelectrical signals in a spectrogram based on the threshold range,
    wherein the o-ERPs are produced by voluntary eye movement when the user's eyes are closed but not when the user's eyes are open or voluntary eyelid squeezing when the user's eyes are closed but not when the user's eyes are open, as a response to the signal sequence; and
    initiate a sleep diary, execute sound control, or start sleep induction with the computational unit based on the existence and the patterns of the o-ERPs.

2. The method of claim 1, wherein the signal sequence comprises sending vibration to the user or playing sound to the user.

3. A method of monitoring ocular event-related potentials (o-ERPs) using an interactive system that includes a computational unit and a bioelectrical signal acquisition device, comprising:
    recording digital bioelectrical signals from a user's head using the bioelectrical signal acquisition device; and
    processing the digital bioelectrical signals with the computational unit to identify the existence and the pattern of ocular event-related potentials (o-ERPs) by:
        applying a Fourier transform to data derived from the digital bioelectrical signals to generate a frequency-domain presentation, and
        identifying the existence and the pattern of the o-ERPs by setting a threshold range and analyzing the digital bioelectrical signals based on the threshold range in the frequency-domain presentation,
    wherein the o-ERPs are produced by voluntary eye movement when the user's eyes are closed but not when the user's eyes are open or voluntary eyelid squeezing when the user's eyes are closed but not when the user's eyes are open, as a response to a signal sequence provided to the user by the computational unit.

4. The method of claim 3, wherein providing the signal sequence to the user comprises sending vibration to the user, playing sound to the user, or applying light to the user.

5. The method of claim 3, wherein the signal sequence includes: a description, a question, or an instruction, all relating to upcoming interactions between the user and the interactive system.

6. The method of claim 5, wherein the signal sequence includes an instruction, and the instruction includes information on how to provide a response by the user.

7. The method of claim 6, wherein providing a response includes an eye movement or an eyelid squeezing by the user.

8. The method of claim 3, wherein the signal sequence comprises a plurality of sounds, and the plurality of sounds include one or more rhythmic audio templates.

9. The method of claim 8, wherein the one or more rhythmic audio templates have a rhythmic frequency between 0.5 Hz and 4 Hz.

10. The method of claim 3, wherein the digital bioelectrical signals have a sample rate ranging from 100 samples per second to 10000 samples per second.

11. The method of claim 3, wherein processing the digital bioelectrical signals further includes a filtering process, which includes using a low-pass filter, a high-pass filter, or a band-pass filter to filter the digital bioelectrical signals.

12. A method of human-computer interaction using an interactive system that includes a computational unit and a bioelectrical signal acquisition device, comprising:
    playing series of rhythmic audio signals to the user with the computational unit;

recording digital bioelectrical signals from the user's head using the bioelectrical signal acquisition device;

processing the digital bioelectrical signals with the computational unit to identify the existence and the pattern of ocular event-related potentials (o-ERPs) by:

applying a Fourier transform to data derived from the digital bioelectrical signals to generate a frequency-domain presentation, and identifying the existence and the pattern of the o-ERPs by setting a threshold range and analyzing the digital bioelectrical signals based on the threshold range in the frequency-domain presentation, wherein the o-ERPs are produced by the user by voluntary eyelid squeezing when the user's eyes are closed but not when the user's eyes are open, as a response to the series of rhythmic audio signals; and inducing the user to fall asleep by providing audio instructions to the user with the computational unit based on a selection corresponding to the existence and the patterns of the o-ERPs that have a same pace as the series of rhythmic audio signals.

13. The method of claim 12, wherein the rhythmic audio signals include sounds of beats, metronome, ding, chirp, ticking, or music pattern.

* * * * *